United States Patent [19]

Starnes et al.

[11] Patent Number: 5,501,968
[45] Date of Patent: Mar. 26, 1996

[54] THERMOSTABLE CYCLODEXTRIN GLYCOSYL TRANSFERASE AND PROCESSES USING IT

[75] Inventors: Robert L. Starnes, Sacramento, Calif.; Philip C. Trackman, Needham, Mass.; Dennis M. Katkocin, New Fairfield, Conn.

[73] Assignee: Novo Nordisk A/S, Bagsvaerd, Denmark

[21] Appl. No.: 66,813

[22] Filed: May 24, 1993

Related U.S. Application Data

[63] Continuation-in-part of Ser. No. 25,529, Mar. 3, 1993, abandoned, and a continuation-in-part of Ser. No. 4,178, Jan. 13, 1993, and a continuation-in-part of Ser. No. 455,188, Dec. 22, 1989, said Ser. No. 25,529, is a continuation-in-part of Ser. No. 337,794, Apr. 13, 1989, and a continuation-in-part of Ser. No. 4,178, said Ser. No. 337,794, which is a continuation at PCT/DK88/00168, Oct. 14, 1988, and is a continuation-in-part of Ser. No. 108,469, Oct. 15, 1987, abandoned, said Ser. No. 4,178, is a continuation of Ser. No. 337,795, Apr. 13, 1989, abandoned, which is a continuation-in-part of PCT/DK88/00168, Oct. 14, 1988, and which is a continuation-in-part of Ser. No. 108,688, Oct. 15, 1987, abandoned.

[51] Int. Cl.$^6$ ............................... C12N 9/10; C12P 19/18
[52] U.S. Cl. ..................... 435/193; 435/97; 435/99; 435/101; 435/210; 435/842
[58] Field of Search ........................ 435/97, 210, 193, 435/99, 101, 842

[56] References Cited

U.S. PATENT DOCUMENTS

| | | | |
|---|---|---|---|
| 3,827,938 | 8/1974 | Farum et al. | 195/62 |
| 3,923,598 | 12/1975 | Horikoshi et al. | 195/31 |
| 3,988,206 | 10/1976 | Shiosaka | 195/62 |
| 4,135,977 | 1/1979 | Horikoshi et al. | 195/7 |
| 4,385,117 | 5/1983 | Ljungdahl et al. | 435/161 |
| 4,418,144 | 11/1983 | Okada et al. | 435/96 |
| 4,477,568 | 10/1984 | Jokse et al. | 435/97 |
| 4,604,355 | 8/1986 | Outtrup | 435/95 |
| 4,628,028 | 12/1986 | Katkocin et al. | 435/95 |
| 4,632,905 | 12/1986 | Starnes et al. | 435/189 |
| 4,929,557 | 5/1990 | Antranikian et al. | 435/202 |

FOREIGN PATENT DOCUMENTS

| | | |
|---|---|---|
| 52-25043 | 2/1977 | Japan . |
| 60-120984 | 6/1985 | Japan . |
| 62-232381 | 10/1987 | Japan . |
| WO89/01043 | 2/1988 | WIPO . |
| WO88/08031 | 10/1988 | WIPO . |
| WO89/01044 | 2/1989 | WIPO . |

OTHER PUBLICATIONS

Chemical Abstracts, vol. 98, No. 85257k, R. W. Mitchell et al., Mar. 14, 1983.
Chemical Abstracts, vol. 111, No. 230637c, C. Yang et al., 1989.
Abstract, Japanese Publication No. JP 60186279, WPI Acc No.: 85–273641/44.
E. K. C. Yu et al., Appl. Microbiol. Biotechnol., vol. 28, pp. 377–379, 1988.

*Primary Examiner*—Herbert J. Lilling
*Attorney, Agent, or Firm*—Steve T. Zelson; Elias J. Lambiris

[57] ABSTRACT

Novel cyclodextrin glycosyl transferases (CGTase) can be produced by anaerobic cultivation of strains of Thermoanaerobacter or Thermoanaerobium. They are more thermostable than known CGTases and have temperature optimum about 95° C.

The novel CGTases can be used for starch liquefaction at pH 4.5 and temperature exceeding 100° C. in the production of dextrose or ethanol. They can also be used for conversion of liquefied starch to cyclodextrin at a temperature of 80°–90° C.

A method for enzymatically converting solid and liquefied starch into cyclodextrin using cyclodextrin glycosyl transferases (CGTase) elaborated by thermophilic obligate anaerobic strains belonging to the genus Clostridium. These CGTases are characterized by thermostability and a capability to liquefy starch and/or to convert liquefied starch to cyclodextrin at pH 5.0–5.5 and 60°–90° C.

5 Claims, 11 Drawing Sheets

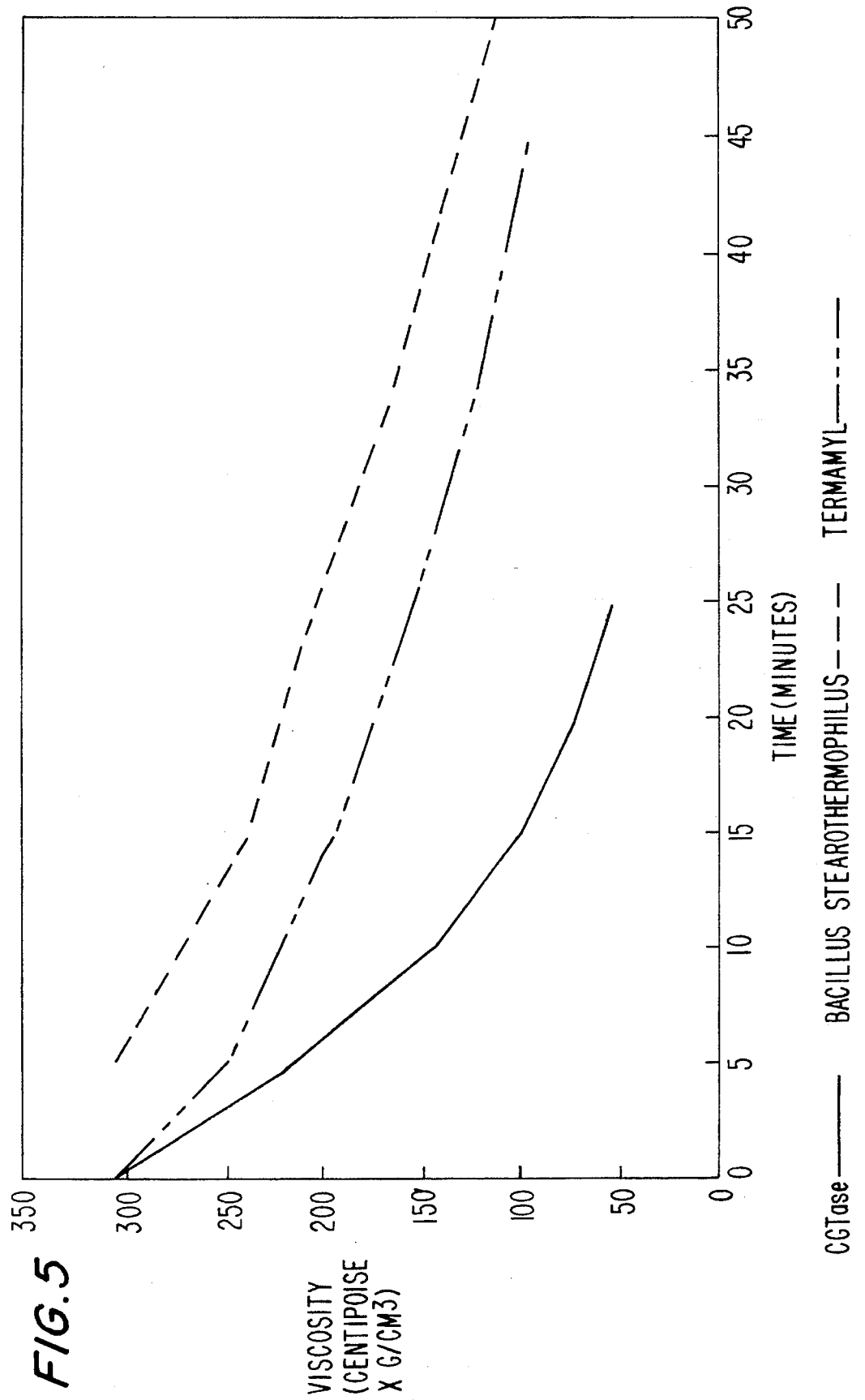

ALPHA-AMYLASE

CGTase

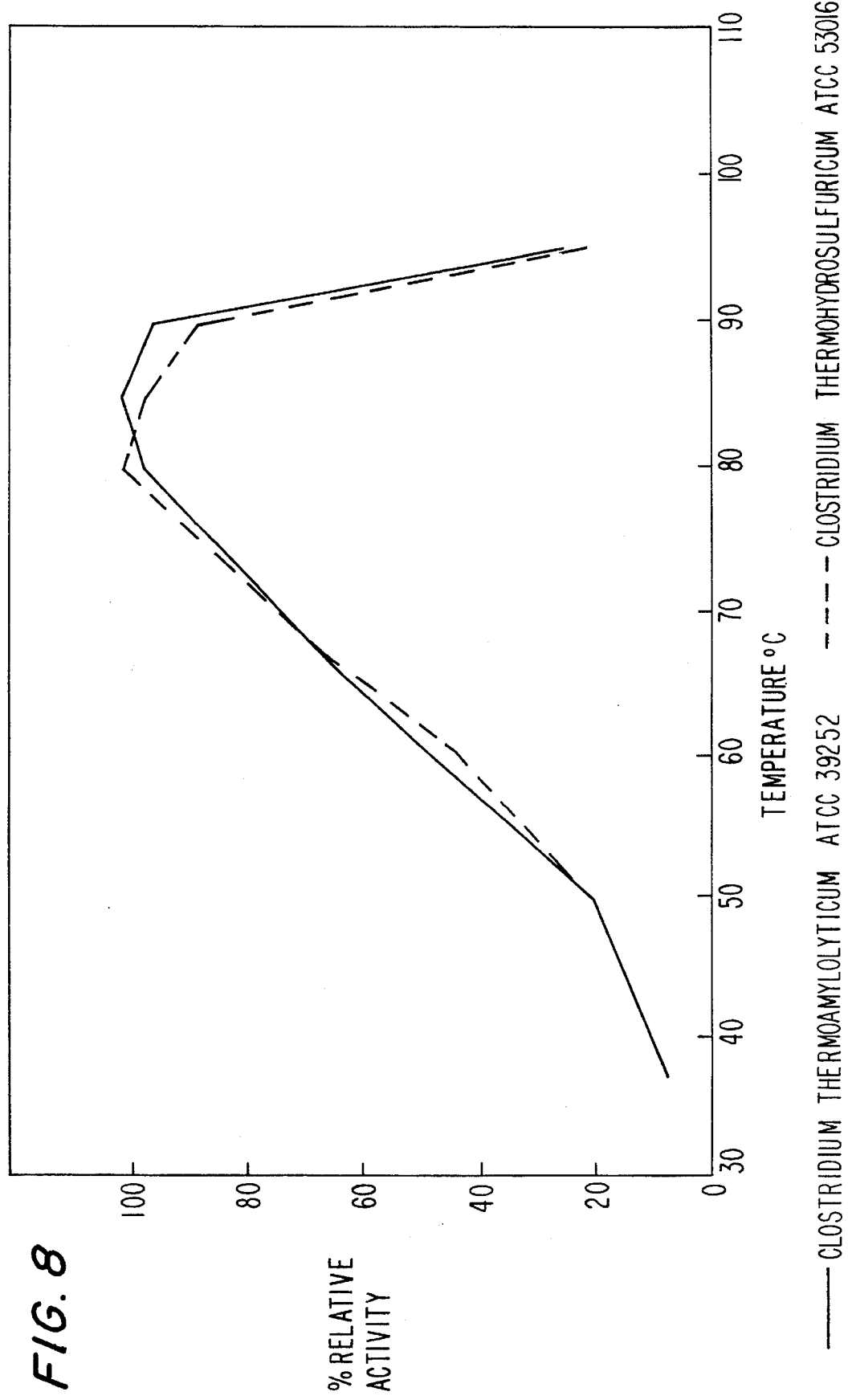

THERMOSTABLE CYCLODEXTRIN GLYCOSYL TRANSFERASE AND PROCESSES USING IT

REFERENCE TO RELATED APPLICATIONS

This application is a continuation-in-part of Ser. No. 08/025,529 filed Mar. 3, 1993, abandoned, Ser. No. 08/004,178 filed Jan. 13, 1993 and Ser. No. 07/455,188 filed Dec. 22, 1989.

Ser. No. 08/025,529 is a continuation-in-part of Ser. No. 07/337,794 filed Apr. 13, 1989 and Ser. No. 09/004,178 filed Jan. 13, 1993.

Ser. No. 07/337,794 is a continuation-in-part of PCT/DK 88/00168 filed Oct. 14, 1988 and Ser. No. 07/108,469 filed Oct. 15, 1987, abandoned.

Ser. No. 08/004,178 is a continuation of Ser. No. 07/337,795 filed Apr. 13, 1989, abandoned, which is a continuation-in-part of PCT/DK 88/00168 filed Oct. 14, 1988 and Ser. No. 07/108,688 filed Oct. 15, 1987, abandoned.

TECHNICAL FIELD

This invention relates to a thermostable cyclodextrin glycosyl transferase (CGTase), to a method for producing it, to a microbial strain capable of producing it, and to processes of using a thermostable CGTase for liquefying starch and for producing cyclodextrin, glucose and ethanol.

BACKGROUND ART

Cyclodextrins, also known as Schardinger dextrins, are starch-derived cyclic compounds containing six, seven, or eight α-D-glucopyranose residues linked by α-1,4 bonds. They are known as α-, β-, γ-cyclodextrin depending on the number of glucose residues, 6, 7 or 8, respectively. These cyclized molecules have neither a non-reducing nor reducing end-group. The cyclic nature of these compounds produces a cavity which is predominantly hydrophobic enabling the formation of inclusion complexes with a number of compounds. This complexation ability is of particular interest to the food, agrochemical, cosmetic, and pharmaceutical industries for: taste masking, stabilization, increasing solubility, powdering, color masking, and emulsification, to name a few possible uses.

A starch solution can be degraded into cyclodextrin by enzymes known as cyclodextrin glycosyl transferases (1,4-alpha-D-glucan 4-alpha-D-(1,4-alpha-D-glucano)-transferase, E. C. 2.4.1.19), hereinafter termed cyclodextrin glycosyl transferase or CGTase. The CGTase enzymes degrade the liquefied starch by catalyzing cyclization and disproportionation reactions.

Typically, cyclodextrin has been prepared heretofore by variations of the method described by E. B. Tilden and C. S. Hudson (J. American Chemical Society) 64:1432[ 1942, which method involves treating liquefied starch with a cyclodextrin glycosyl transferase (CGTase) enzyme from *Bacillus macetans*. All variations of this process have a number of disadvantages. First, since the CGTase is not sufficiently thermostable to be used above the gelatinization temperature of starch, the starch must be pretreated, e.g., with an α-amylase, to solubilize the starch. It is important that the starch be liquefied to a relatively low DE (Dextrose Equivalent), so after conduct of the starch liquefaction process, the treating agent, normally an α-amylase, must be inactivated, to obtain good cyclodextrin yield. Second, the *Bacillus macerans* CGTase is not sufficiently stable to be used at elevated temperatures, and consequently, the enzymatic cyclodextrinization process is carried out at about 50° C., where it is subject to possible microbial contamination. Third, conversion of starch to cyclodextrin (at 50° C., pH 7.0) by the Bacillus macerans CGTase requires extended reaction time, before reasonable yields are achieved.

Importantly, reactions catalyzed by CGTase which cleave the starch molecule can generate a desirable viscosity reduction in liquefied starch solutions by lowering the average molecular weight of the dextrin in the solution (without, in the instance of the CGTase, generating reducing sugars). The CGTase enzymes previously known to the art were produced by such microorganisms as *Bacillus macerans, Bacillus circulans, Bacillus stearothermophilus, Bacillus megaterium, Bacillus ohbensis,* alkalophilic Bacillus sp., *Micrococcus luteus, Micrococcus varians,* and *Klebsiella pneumoniae*. Unfortunately, none of the CGTase enzymes produced by these microorganisms seem to be sufficiently thermostable for use in industrial-scale for a combination of starch liquefaction and cyclodextrin production at temperatures sufficiently elevated to avoid possible microbial contamination.

Enzymatic liquefaction of aqueous starch slurry is widely practiced as the first step in converting starch to dextrose (glucose). To a great extent the starch industry has adopted the liquefaction process of U.S. Pat. No. 3,921,590. Typical conditions are jet cooking at 105° C. for 5 minutes, followed by a 90 minute hold at 95° C., at a starch concentration of 35% DS (dry substance), by weight. The enzyme used in this process is Termamyl™ (product of Novo Industri A/S), an α-amylase from *Bacillus licheniformis*. Liquefaction is performed at pH about 6.0, followed by saccharification with glucoamylase at a pH of approx 4.5–5.0.

The art has long sought starch liquefaction enzymes capable of liquefying at pH 4.5, in order to eliminate the need for intermediate pH adjustment. α-amylase from *Bacillus stearothermophilus* has been suggested for this purpose, but data in this specification show that it does not liquefy well at pH as low as 4.5. U.S. Pat. No. 4,578,532 and U.S. Pat. No. 4,613,570 disclose aciduric α-amylases from Clostridium, but data in said patents show that their stability at 100° C. or above at pH 4.5 is insufficient.

OBJECT OF THE INVENTION

It is an object of this invention to provide a cyclodextrin glycosyl transferase with sufficient heat stability to be used for CD production at 60° C. or higher, where the risk of microbial infection is slight, and even to be used for starch liquefaction above 90° C., where the starch is fully gelatinized. It is also an object of the invention to provide an enzyme capable of liquefying starch at pH 4.5 and a temperature above 100° C.

It is also an object of the invention to provide a method of using a thermostable CGTase for producing cyclodextrin. Other objects of the invention are the provision of a method of producing said thermostable enzyme and a microbial strain capable of producing it. It is a further object to provide a process using said enzyme to produce CD at 60° C. or higher and a process using said enzyme for starch liquefaction at a pH around 4.5–5.0.

SUMMARY OF THE INVENTION

The inventors have isolated a number of thermophilic obligate anaerobic strains that produce CGTases of surprising heat stability.

Accordingly, in its first aspect the invention provides a cyclodextrin glycosyl transferase, characterized in that it is native to a strain of Thermoanaerobacter or Thermoanaerobium, has a temperature optimum measured at pH 5.0 of about 95 ° C.; a pH optimum of about 5.0; and a residual activity after 40 minutes incubation at 80° C. and pH 5.0 of about 95% in the absence of starch and $Ca^{++}$.

A second aspect of the invention provides a method for producing a cyclodextrin glycosyl transferase (CGTase) comprising cultivation of a CGTase producing strain of Thermoanaerobacter or Thermoanaerobium under anaerobic conditions, or cultivation of a transformed host organism containing the appropriate genetic information therefrom under aerobic conditions, in a suitable nutrient containing medium and thereafter recovering CGTase from the fermentation medium.

A third aspect of the invention provides a biologically pure culture of a strain of Thermoanaerobacter or Thermoanaerobium, characterized by the ability to produce cyclodextrin glycosyl transferase, and by being non-motile.

A fourth aspect of the invention provides a starch liquefaction process which comprises subjecting an aqueous starch slurry to enzymatic liquefaction in the presence of said cyclodextrin glycosyl transferase at a pH in the range of about 4.0 to 5.5 preferably at a temperature exceeding about 100° C.

A fifth aspect of the invention provides a process for producing cyclodextrin which comprises enzymatically treating a starch hydrolysate solution with said cyclodextrin glycosyl transferase, at a temperature of above 60° C. and thereafter recovering a cyclodextrin product from the reaction mixture.

Finally, a sixth aspect of the invention provides a process for producing cyclodextrin which comprises enzymatically treating an aqueous starch slurry with the cyclodextrin glycosyl transferase of Claim 1 at a temperature of above about 100° C. and at a pH in the range of 4.0–5.5, preferably essentially without addition of a calcium salt, thereafter holding the resulting syrup at a temperature in the range of 80°–90° C. for not more than about 28 hours, the syrup being in the range of 20–30 DS during at least part of said hold period, and then recovering a cyclodextrin product from the reaction mixture.

Furthermore, thermostable CGTase enzymes produced by strains of the thermophilic obligate anaerobic microorganisms *Clostridium thermoamylolyticum* ATCC 39,252 and *Clostridium thermohydrosulfuricum* ATCC 53,016 have been discovered. These CGTase enzymes are usable at pH 5.0–5.5 and 105° C.

U.S. Pat. No. 4,578,352 and U.S. Pat. No. 4,613,570 describe aciduric alpha-amylase enzymes from these two strains. Unfortunately, the strains produce the CGTase enzymes in such low yield that the inventors hereof are unable to ascertain whether the aciduric alpha-amylase compositions disclosed in U.S. Pat. Nos. 4,578,352 and 4,613,570 contained CGTase. However, the use of enzymes from these strains in production of cyclodextrin is novel and could not be predicted.

A number of thermophilic anaerobic microorganisms have been investigated in the prior art for unique, thermostable enzymes. Notably, species of the genus Clostridium have been the focus of attention including *Clostridium thermoamylolyticum, C. thermohydrosulfuricum, C. thermocellum, C. thermosaccharolyticum, C. thermoaceticum, C. thermosulfurogenes, C. stercorarium,* and *C. fervidus*. However, none of the Clostridium strains have been reported to produce a thermostable cyclodextrin glycosyl transferase, probably because CGTases were not being sought.

Accordingly, the invention provides an enzymatic process for converting a preliquefied starch into cyclodextrin with a Clostridium species CGTase enzyme followed by recovery of cyclodextrin.

A further aspect of this invention provides a process for converting solid starch into cyclodextrin which comprises liquefying the starch with the CGTase enzyme under typical starch liquefaction conditions which, for example, may be under the time and temperature liquefaction conditions used in the high-fructose corn syrup industry followed by enzymatic conversion of the liquefied starch with the CGTase enzyme and recovery of cyclodextrin.

The process of this invention has a number of advantages. First, the starch does not need to be preliquefied, e.g., with an alpha-amylase to solubilize the starch. Second, the CGTase is sufficiently stable at above 60° C. to be used at such higher temperatures, avoiding thereby possible microbial contamination. Third, the conversion of starch to cyclodextrin does not require extended reaction times before reasonable yields are achieved.

BRIEF DESCRIPTION OF DRAWINGS

FIG. 5 is a viscosity versus time plot comparing starch liquefaction with the CGTase, Termamyl™ and *Bacillus stearothermophilus* α-amylase;

FIG. 8 is a plot of relative activity versus temperature for the CGTase;

DETAILED EXPLANATION OF THE INVENTION

Microorganism

Figure 1:
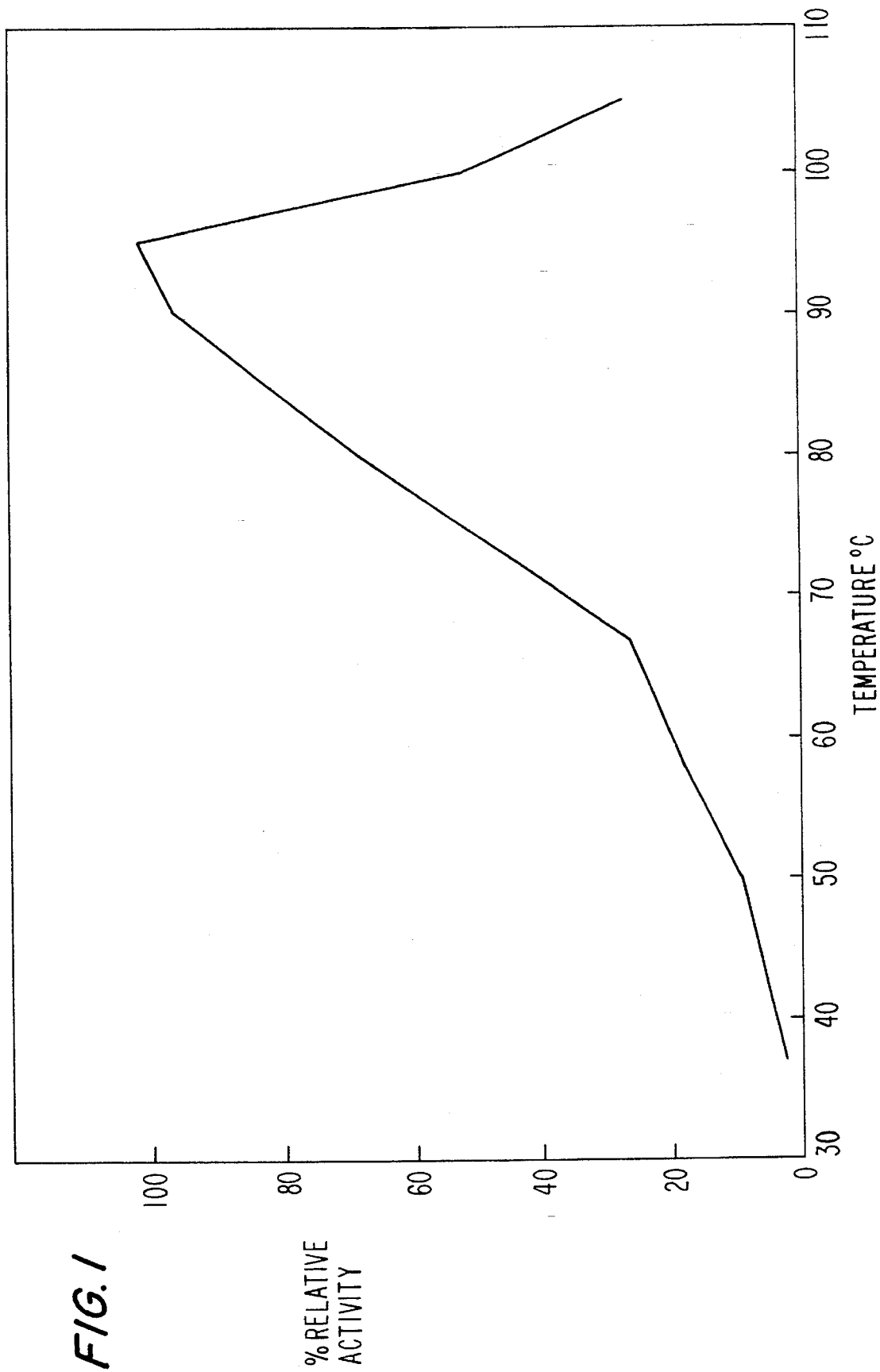
FIG. 1 is a plot of relative activity versus temperature for the CGTase.

The microorganisms of the invention are thermophilic obligate anaerobic bacteria belonging to the genus Thermoanaerobacter (J. Wiegel and L. G. Ljungdahl, Arch. Microbiol. (1981) 128: 343–348) or the genus Thermoanaerobium (J. G. Zeikus et al., Arch. Microbiol., 122, 41–48 (1979). The taxonomy for these genera is not established, and it is considered likely that the two genera could properly be classified as one and the same genus, since they are so similar that even an expert in this field cannot differentiate them.

In contrast to known strains of Thermoanaerobacter and Thermoanaerobium, the microbial strains of the invention are characterized by the ability to produce CGTase and by being non-motile. Some strains of the invention are also indole positive, in contrast to known strains. Known strains T. ethanolicus DSM 3389 and T. fini DSM 2246 were found not to be producers of thermostable CGTase.

8 strains were isolated by the inventors and were deposited at the American Type Culture Collection (ATCC) and the National Collections of Industrial Marine Bacteria (NCIMB) for parenting purposes under the terms of the Budapest Treaty, as follows:

|   | Deposit No. | Deposit Date | Depositor's Reference |
|---|---|---|---|
| 1. | ATCC 53,627 | June 3, 1987 | ANO-15-7-5A2-70 |
| 2. | NCIB 40,053 | October 6, 1988 | ANO-16-7-2A-70 |
| 3. | NCIB 40,054 | October 6, 1988 | ANO-16-7-4A-70 |
| 4. | NCIB 40,055 | October 6, 1988 | ANO-36-7-1 |
| 5. | NCIB 40,056 | October 6, 1988 | ANO-38-7-1 |
| 6. | NCIB 40,057 | October 6, 1988 | ANO-44-5-1-55 |
| 7. | NCIB 40,058 | October 6, 1988 | ANO-51-7-1-70 |
| 8. | NCIB 40,059 | October 6, 1988 | ANO-55-7-1-70 |

Mutants and variants of the above strains are also within the scope of the invention.

These 8 strains were all classified by NCIMB, Scotland, as Thermoanaerobactersp. or Thermoanaerobium sp., the genus being unresolved. Further taxonomic data are given below:

| Strain No. | 1 | 2 | 3 | 4 | 5 | 6 | 7 | 8 |
|---|---|---|---|---|---|---|---|---|
| °C. incubation | 55 | 60 | 60 | 60 | 60 | 60 | 60 | 60 |
| Cell morphology |  |  | (a) |  |  |  | (b) |  |
| Gram | − | − | − | − | − | − | − | var. |
| Spores | − | − | − | − | − | − | − | − |
| Motility | − | − | − | − | − | − | − | − |
| Colonial Morphology | (c) |  | (d) |  | (d) |  | (d) | (d) |
| Growth |  |  |  |  |  |  |  |  |
| 30° C. | (e) |  |  |  |  |  |  |  |
| 37° C. | ND | ND |  | + |  |  |  |  |
| 50° C. | + |  |  |  |  |  |  |  |
| Viscous in KOH test | + | + | + | + | + | + | + | + |
| Growth Glucose Ye | (+) | + | + | + | + | − | − | + |
| Growth TYG | + | ND | ND | + | ND | − | − | + |
| Catalase | − | − | − | − | − | − | − | − |
| Oxidase, Kovacs P-W-S | (f) | − | − | − | − | − | − | − |
| Chloramphenicol sensitivity | + |  |  |  |  |  |  |  |
| Hemolysis on horse blood agar | − |  |  |  |  |  |  |  |
| Litmus milk reduction PNPG | + |  |  |  |  |  |  |  |
| $H_2S$ production | + |  |  |  |  |  |  |  |

See notes (a)–(f) below:
(a) Granular rods of varying length, in chains.
(b) Regular rods, 'granular' staining, singly and in short chains.
(c) (starch agar, 3 days): round, regular, entire, smooth, low (?), convex (?), opaque, yellowish-buff, 2.5 mm diameter.

(d) (R.C.M., 3 days): round, regular, entire, smooth, shiny, translucent, flat, white, 3 mm diameter.
(e) + (slow 7 days).
(f) Peptone Water Sugar: No acid or gas.
ND Not determined

| | API 20A Anaerobic Test 24 hours 60° C. | | | | | | | |
|---|---|---|---|---|---|---|---|---|
| Strain No. | 1 | 2 | 3 | 4 | 5 | 6 | 7 | 8 |
| Indole | + |  |  | − | − | − |  |  |
| Urease |  | NC | NC | − | − | − | NC | NC |
| Acid from: |  |  |  |  |  |  |  |  |
| Glucose |  |  |  | − | − | − |  |  |
| Mannitol |  |  |  | − | − | − |  |  |
| Lactose |  |  |  | − | − | − |  |  |
| Sucrose |  |  |  | + | − | − |  |  |
| Maltose |  |  |  | + | − | + |  |  |
| Salicin |  |  |  | + | − | − |  |  |
| Xylose |  |  |  | + | + | + |  |  |
| Arabinose |  |  |  | − | − | + |  |  |
| Glycerol |  |  |  | − | − | − |  |  |
| Cellobiose |  |  |  | ± | − | + |  |  |
| Mannose |  |  |  | + | − | + |  |  |
| Melezitose |  |  |  | − | − | − |  |  |
| Raffinose |  |  |  | − | − | − |  |  |
| Sorbitol |  |  |  | − | − | − |  |  |
| Rhamnose |  |  |  | − | − | + |  |  |
| Trehalose |  |  |  | ± | (+) | + |  |  |
| Gelatinase* |  |  |  | − | + | + |  |  |
| Aesculin hydrolysis |  |  |  | + | + | + |  |  |

NC No change after incubation
± Trace reaction
*May be artefact caused by high temperature Production of CGTase derived from Thermoanaerobacter or Thermoanaerobium The preparation of the CGTase enzyme may be accomplished by culturing a microbial strain of the invention (for example ATCC 53,627) under anaerobic conditions in a medium which contains maltodextrin as the carbon source, yeast extract, and mineral solutions. The optimum pH and temperature for production of the CGTase is pH 7.0 and 67° C. The enzyme is excreted into the fermentation medium indicating it is an extracellular enzyme.

Alternatively, CGTase of the invention can be produced by aerobic cultivation of a transformant containing the appropriate genetic information. In general, this method of production will comprise the following steps:

(a) providing a suitable recombinant DNA cloning vector comprising DNA sequences encoding functions facilitating gene expression and a DNA sequence encoding the CGTase of a Thermoanaerobacter or Thermoanaerobium strain;

(b) transforming a suitable host organism with the cloning vector from step (a);

(c) cultivating the transformed host under aerobic conditions in a suitable nutrient containing medium and thereafter recovering CGTase from the medium Examples of suitable host organisms are strains of Escherichia, Streptomyces, Bacillus or Aspergillus, preferably a strain of E. coli, B. subtills, B. licheniformis or A. oryzae.

The CGTase can be recovered by removing the cells from the fermentation medium and then concentrating the broth, e.g. by ultrafiltration.

Production of CGTase derived from Clostridium

CGTase for use in processes of this invention can be produced by the thermophilic obligate anaerobic bacteria *C. thermoamylolyticum* ATCC 39,252 and *C. thermohydrosulfuricum* ATCC 53,016. The CGTases are extracellular enzymes. Both of these strains were known to the art prior to this invention, having been reported as source microorganisms for an aciduric alpha-amylase.

The microorganisms were cultured and maintained using standard anaerobic methodology. Production of the CGTase was achieved by culturing the microorganisms in a pre.reduced liquid medium under argon comprised of the following components in grams pegr liter: Maltrin M-100, 8.0; $KH_2PO_4$, 1.5; $Na_2HPO_4 \cdot 12H_2O$, 4.2; $NH_4Cl$, 0.5; $MgCl_2 \cdot 6H_2O$, 0.18, yeast extract, 2.0; $Na_2S$, 0.5; cysteine-HCl, 0.5; resazurin (redox indicator), 2 ng; and trace metals 5.0 ml. The trace metal solution was comprised of the following components in grams per liter: $FeCl_3 \cdot 6H_2O$, 5.40; $ZnSO_4 \cdot 7H_2O$, 1.45; $MnCl_2 \cdot 4H_2O$, 1.00; $CuSO_4 \cdot 5H_2O$, 0.25; and $H_3BO_3$, 0.10. The trace metals solution was acidified with concentrated HCl to dissolve the salts. The strains were grown at 55° C. for 24–20 hours (initial pH 7.0). The CGTases are produced extracellularly and were recovered from the cell-free broth using methods known to the art.

*C. thermoamylolyticum* ATCC 39,252 and *C. thermohydrosulfuricum* ATCC 53,016 both produced levels of CGTase sufficient for characterization.

Purification of CGTase

For characterization purposes, purification of the crude CGTase preparation from ATCC 53,627 to homogeneity was achieved by DEAE-Sepharose chromatography, Chromatofocusing®, and acarbose-Sepharose affinity chromatography. Three components designated I, II and III were purified. Only one CGTase component was found in the crude preparations from the other strains, based on SDS-polyacrylamide gel electrophoresis.

Thermostability of CGTase

CGTases of the invention are characterized by thermostability far superior to prior art enzymes. After incubation in 5% Lintnet starch—0.1 M sodium acetate pH 5.0 (50 ppm $Ca^{++}$)—for 50 minutes at 95° C., CGTase of the invention (ATCC 53,627) retains nearly 100% of its activity.

Figure 3:
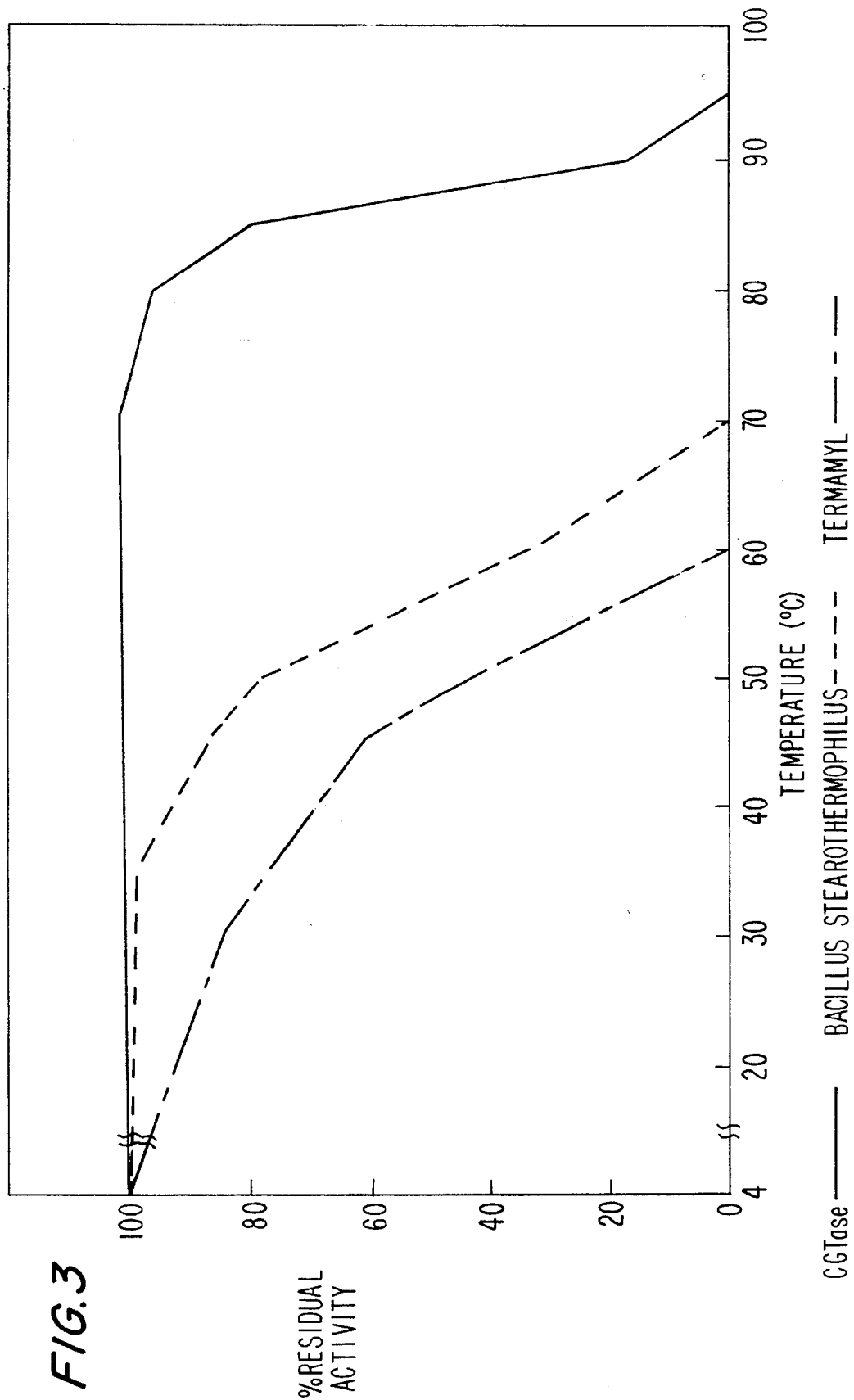
FIG. 3 is a plot of the thermostability of CGTase from ATCC 53,627 relative to *Bacillus stearothermophilus* α-amylase and Termamyl™.

FIG. 3 shows the residual activity of crude CGTase from ATCC 53,627 after 40 minutes incubation at various temperatures at pH 5.0 in the absence of substrate and $Ca^{++}$. As shown, it retains approx. 95% of its activity at 80° C. at these conditions. For comparison, data for two prior-art liquefying enzymes are also shown: α-amylase from *Bacillus licheniformis* (Termamyl™) and α-amylase from *Bacillus stearothermophilus*.

Components I, II and III have similar thermostability as the crude CGTase of ATCC 53,627. For comparison, the *Bacillus macerans* CGTase is reported to be stable only at temperatures below 50° C. and to lose activity rapidly at above 50° C. (Stavn, A. and Granum, P. E. in Carbohydrate Research, 75[ 1979] 243).

Figure 2:
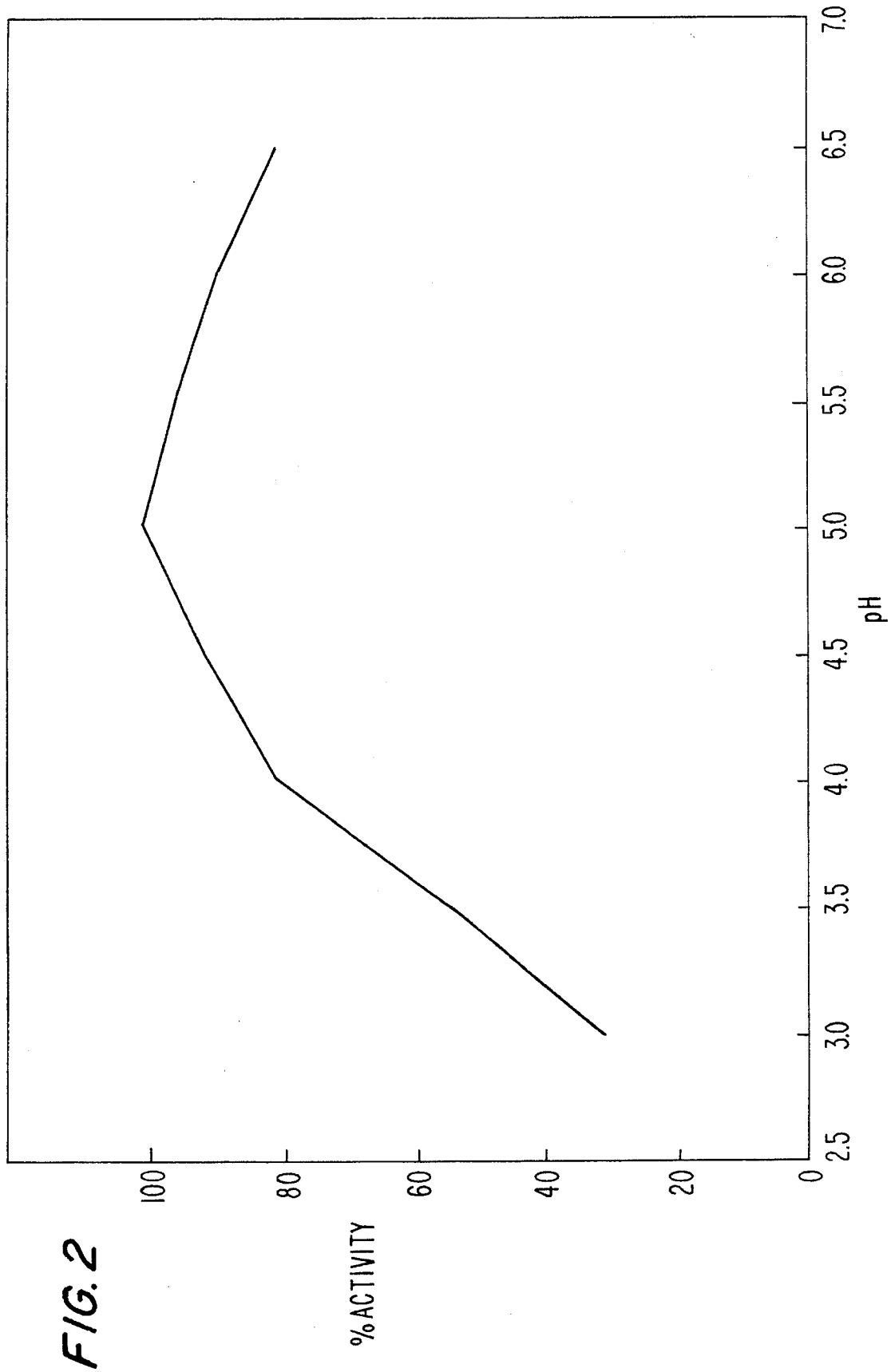
FIG. 2 is a plot of relative activity versus pH for the CGTase.

Characterization of CGTase derived from Thermoanaerobacter or Thermoanaerobium Temperature Optimum. The effect of temperature on CGTase activity was determined. The CGTase from ATCC 53,627 possesses a temperature optimum at 95 ° C. at pH 5.0 in 0.1 M sodium acetate—100 ppm $Ca^{++}$ buffer contrast to that of the *Bacillus macerans* CGTase which is reported to be 55 ° C. at pH 6.0 (Stavn, A. and Granum, P. E. in Carbohydrate Research, 75 [1979]243).

pH Optimum. The effect of pH on CGTase activity was examined at 60° C. The pH optimum of the CGTase from ATCC 53,627 is 5.0 with broad activity in the acidic region when tested in a citrate-phosphate—0.5% Linther starch—100 ppm $Ca^{++}$ buffer system (see FIG. 2). This value is similar to the pH optimum of 5.2–5.7 reported for *Bacillus macerans* CGTase (Stavn, A. and Granum, P. E. in Carbohydrate Research, 75 [1979] 243).

Molecular Weight. The molecular weights of the CGTases, determined by SDS-polyacrylamide gel electrophoresis followed by a 0.8% Linther starch-iodine Gelrite® overlay at pH 6.0, 55° C., were as follows:

| | |
|---|---|
| ATCC 53,627 I | 117,000 Daltons |
| ATCC 53,627 II | 110,000 - |
| ATCC 53,627 III | 108,000 - |
| NCIB 40,053 | 99,000 - |
| NCIB 40,054 | 106,000 - |
| NCIB 40,055 | 104,000 - |
| NCIB 40,056 | 101,000 - |
| NCIB 40,057 | 126,000 - |
| NCIB 40,058 | 210,000 - |
| NCIB 40,059 | 154,000 - |

These results demonstrate that the CGTases are all different.

Isoelectric Points. Isoelectric focusing employing a LKB Ampholine PAG plate pH 3.5–9.5 followed by a 0.8% Lintner starch iodine agar overlay at pH 6.0, 55° C. has shown that the isoelectric points of CGTase I, II, and III are 4.55, 4.50, and 4.50, respectively.

Figure 4A:
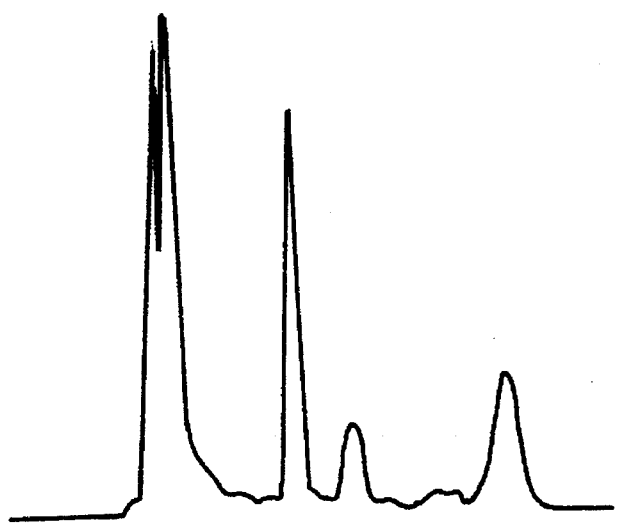
FIG. 4A, 4B and 4C are the HPLC plots showing the action pattern of CGTases I, II, III.
Figure 4B:
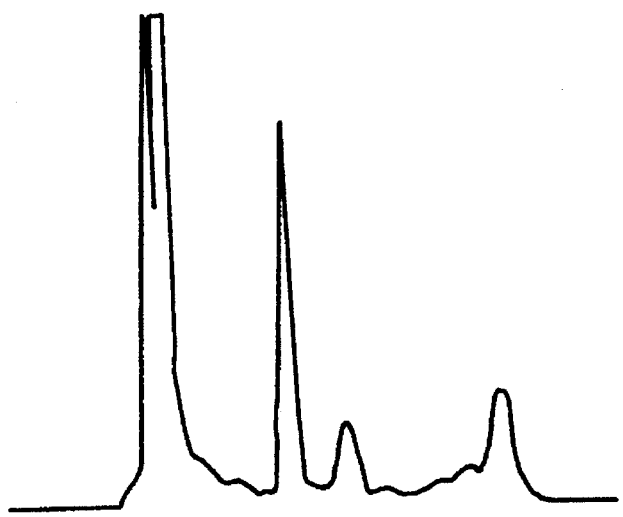
Figure 4C:
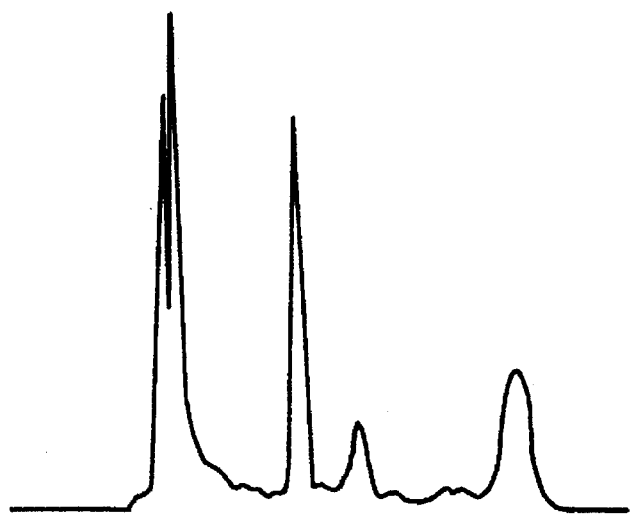

Action Patterns. Aminex® HPX-42A (Bio-Rad) HPLC using refractive index for detection demonstrated that the action patterns produced from degradation of Lintner starch by each CGTase from ATCC 53,627 were identical (see FIG. 4). The three CGTases are, therefore, catalytically the same. The three peaks at the right appear after hydrolysis and have been shown to be (from left to right) α-, γ, and β-cyclodextrin, respectively, by NMR.

Figure 7A:
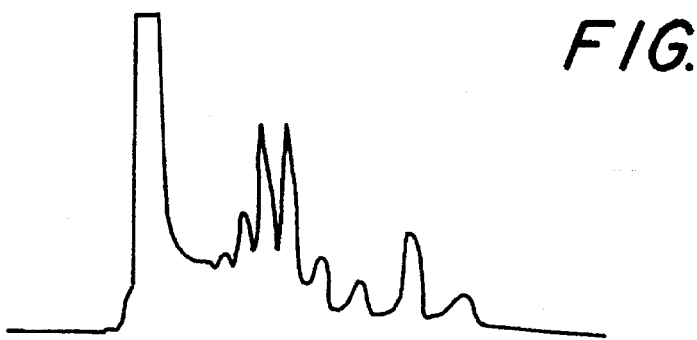
FIG. 7A, and 7B are the HPLC plots comparing the action patterns of the CGTase and the α-amylase of *Bacillus stearothermophilus*.
Figure 7B:

FIG. 7 compares the action pattern produced by CGTase of the invention (ATCC 53,627) with a prior-art liquefying enzyme, viz. α-amylase from *Bacillus stearothermophilus*.

Conversion of Starch to Cyclodextrin. The determination of % conversion to α-, γ-, or β-cyclodextrin during liquefaction with CGTase from ATCC 53,627 at a standard dose of 4.46 Phadebas U/g DS is shown below. The conditions were 35% DS corn starch at pH 4.5 with primary liquefaction at 105° C. for 14 minutes and secondary liquefaction at 90° C. for 4 hours. Also shown is the % conversion for CGTase (6.8 Phadebas U/g DS) with 5% DS Lintner starch—0.1 M sodium acetate (50 ppm $Ca^{2+}$) at pH 5.0 and 95° C. for 50 minutes. In liquefaction equal amounts of α- and γ-cyclodextrin are produced while almost twice as much β-cyclodextrin is formed. In the Lintner starch reaction twice as much β-cyclodextrin is formed as γ-cyclodextrin, however, three times as much α-cyclodextrin is formed as γ-cyclodextrin.

| | Cyclodextrin | | |
|---|---|---|---|
| Reaction | α-CD | γ-CD | β-CD |
| Lintner starch | 13.8 | 4.4 | 9.3 |

-continued

| | Cyclodextrin | | |
|---|---|---|---|
| Reaction | α-CD | γ-CD | β-CD |
| Liquefaction | 3.8 | 3.6 | 6.4 |

Characterization of CGTase derived from Clostridium

Figure 9:
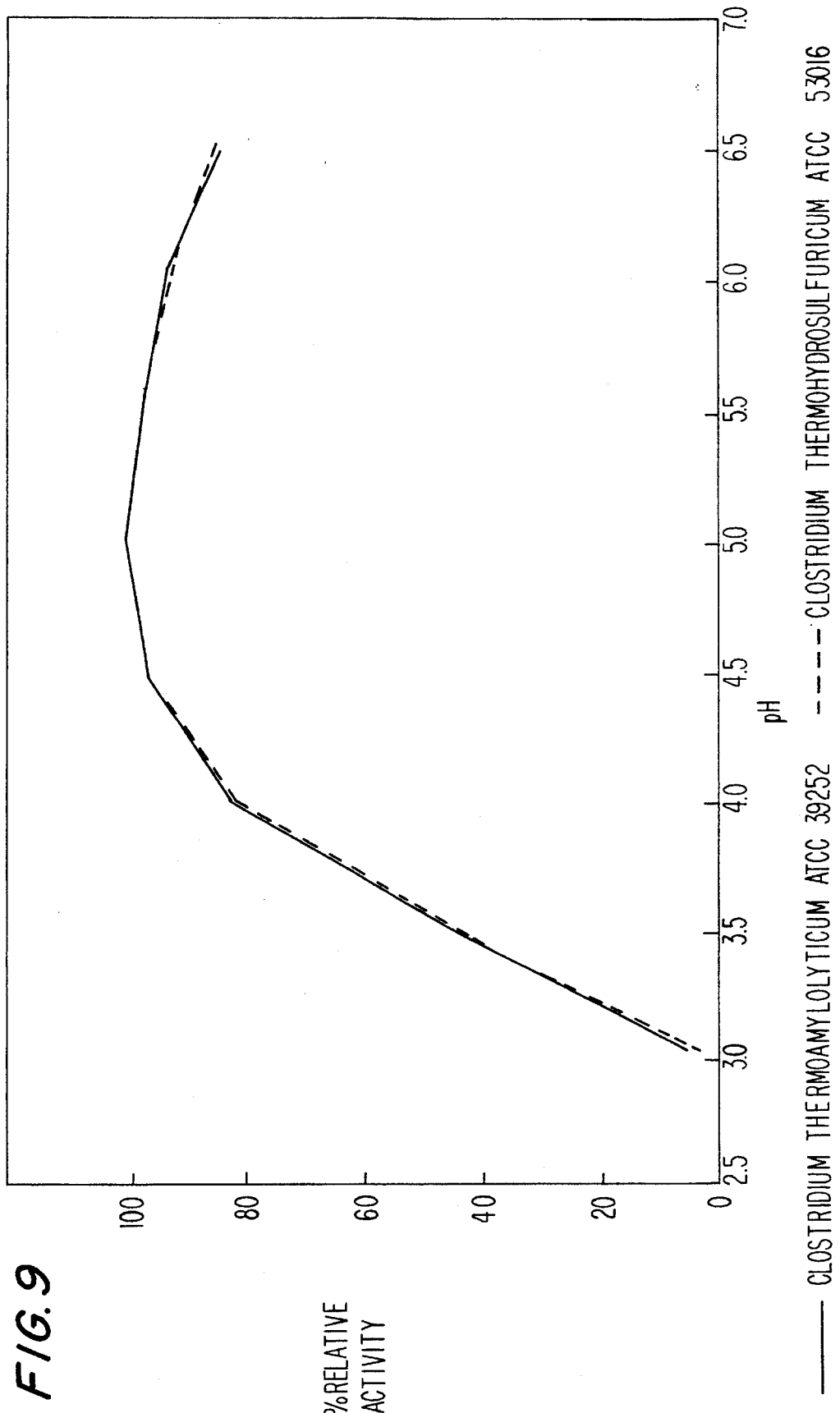
FIG. 9 is a plot of relative activity versus pH for the CGTase.

Temperature optimum. The effect of temperature on the CGTase activities was determined at pH 5.0 in 0.1 M sodium acetate (100 ppm $Ca^{++}$). The *C. thermoamylolyticum* and *C. thermohydrosuifuricum* CGTases possess temperature optimum of 85° C. and 80° C., at pH 5.0, respectively (see FIG. 8).

pH optimum. The effect of pH on the CGTase activities was examined at 60° C. in a citrate-phosphate—0.5% Lintner starch (100 ppm $Ca^{++}$) buffer system. The pH optimum of both CGTases is 5.0 (see FIG. 9).

Molecular weights. The molecular weights of the CGTases were determined by SDS-polyacrylamide gel electrophoresis to be 110 kD for the CGTases from both *C. thermoamylolyticum* and *C. thermohydrosulfuricum*.

Isoelectric points. Isoelectric focusing employing a LKB Ampholine PAG plate pH 3.5–9.5 followed by a 0.8% Lintner starch-iodine overlay at pH 6.0, 55° C. demonstrated that the isoelectric points for both CGTases are 4.8.

Liquefying activity. The starch liquefying activity of the CGTases was determined under simulated industrial conditions. The CGTases were incubated with 35% DS corn starch at either pH 4.5, 5.0, 5.5, or 6.0 for 14 minutes at 105° C. followed by 4 hours at 90° C. The enzyme dose was 4.46 Phadebas units per gram DS starch. The starch was judged as liquefied if it was pourable. Also, dextrose equivalents (DE) were measured by the neocuproine method.

The results, shown in the table below, demonstrated that both CGTases are able to liquefy corn starch at pHs 5.5 and 6.0 while only the *C. thermohydrosuifuricum* CGTase can liquefy at pH 5.0. The DE measurements were less than 1.0 which is consistent with CGTase.

| | Liquefying activity (40 ppm $Ca^{++}$) | |
|---|---|---|
| pH | *Clostridium thermoamylolyticum* | *Clostridium thermohydrosulfuricum* |
| 6.0 | yes | yes |
| 5.5 | yes | yes |
| 5.0 | no | yes |
| 4.5 | no | no |
| 4.5 | no | no |

Figure 10:
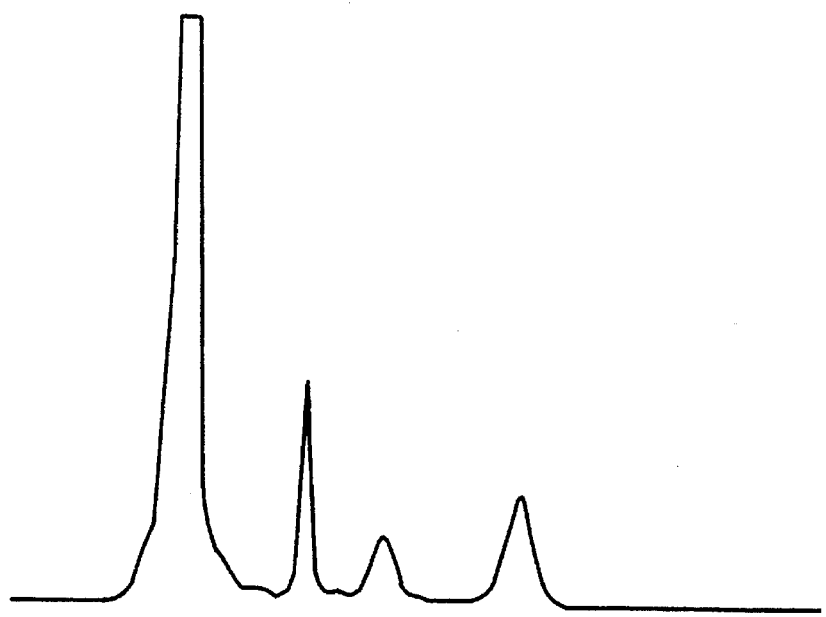
FIG. 10 is an HPLC plot showing the action pattern of CGTase from *Clostridium thermoamylolyticum* ATCC 39,252 at pH 5.5 on 35% DS corn starch.
Figure 11:
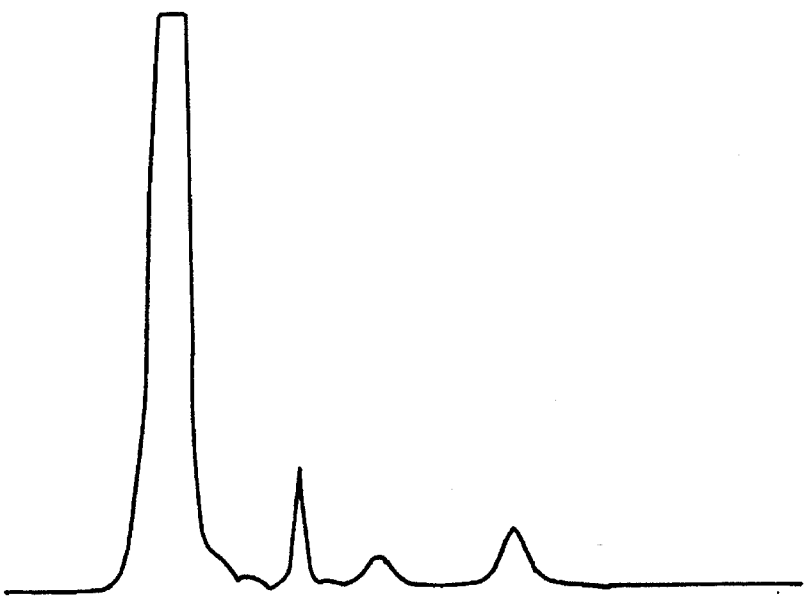
FIG. 11 is an HPLC plot of the action pattern of CGTase from *Clostridium thermohydrosulfuricum* ATCC 53,016 at H 5.0 on 35% DS corn starch.

Action patterns. The action patterns of the liquefied starches produced by the two Clostridium CGTases as determined by Bio-Rad Aminex® Carbohydrate HPX-42A HPLC were characteristic of a CGTase (see FIGS. 10 and 11).

Comparison of Cyclodextrin Glycosyl Transferases

A comparison of CGTase derived from Thermoanaerobacter or Thermoanaerobium with published data on several known CGTases is presented in the table below. Several clear differences are evident, in particular, the temperature optimum and stability.

There are several notable differences between CGTase derived from Clostridium and that derived from Thermoanaerobacter or Thermoanaerobium:

(1) The temperature optimum for the Clostridium CGTases range from 80°–85 ° C. relative to 95° C. for the Thermoanaerobacter CGTase.

(2) The isoelectric point for both Clostridium CGTases is 4.8 which compares to approximately 4.5 for the Thermoanaerobacter CGTase. The molecular weights based on SDS-PAGE are the same.

(3) The Clostridium CGTases are unable to liquefy solid starch at pH 4.5 unlike the Thermoanaerobacter CGTase.

(4) The Clostridium CGTases produce cyclodextrin more favorably from starch that has been partially hydrolyzed to a DE of approximately 7.0. The Thermoanaerobacter CGTase prefers unhydrolyzed starch.

| COMPARISON OF CYCLODEXTRIN GLYCOSYL TRANSFERASES FROM VARIOUS MICROORCANISMS | | | | | | | |
|---|---|---|---|---|---|---|---|
| | Invention ATCC53627 | *Bacillus stearothermophilus* TC-60 | *Bacillus megaterium* | *Bacillus circulans* ATCC9995 | *Bacillus macerans* IFO3490 | *Bacillus sp.* ATCC21783 | *Micrococcus sp.* ATCC31606 |
| Isoelectric point | 4.50,4.55 | 4.50 | 6.07,6.80 | 5.80,6.60 | 4.60 | 5.4 | 4.20 |
| Molecular weight (SDS) | 108,000 110,000 117,000 | 68,000 | 75,000 | | 75,000 | 88,000 | 85,000 |
| Temperature optimum | 95° C. (pH 5.0) | 70° C. (pH 7.0) | 55° C. (pH 7.0) | 55° C. (pH 7.0) | 55° C. (pH 6.0) | 50° C. (pH 7.0) | 55–65° C. (pH 7.0) |
| pH optimum | 5.0 | 6.0 | 5.2–6.2 | 7.0–9.0 | 5.2–5.7 | 4.5–5.0 & 7.5–8.5 | 5.5–6.5 & 10.0 |
| Temperature stability* (Maintains 95–100% activity) | 80° C. (pH 5.0) | 50° C. (pH 7.0) | 55° C. (pH 7.0) | 55° C. (pH 7.0) | 55° C. (pH 6.0) | 60° C. (pH 7.0) | 50° C. (pH 7.0) |

*absence of substrate

Starch Liquefaction Process

Liquefaction of starch serves to partly depolymerize and solubilize starch so as to make it amenable to subsequent enzymatic saccharification, e.g. by glucoamylase. To a great extent the industry has adopted the liquefaction process of U.S. Pat. No. 3,921,590. Typical conditions are heating to 105° C., e.g. by jet cooking, holding for 5 minutes at that temperature followed by a 90 minute hold at 95° C. with *B. stearothermophilus* liquefies well at pH 5.8, but both of said α-amylase are unable to liquefy below pH 5.0. The liquefraction process provided by this invention is made at about pH 4.0–5.5 (preferably 4.5–5.5), whereby subsequent saccharification can be made without intermediate pH adjustment.

CGTase of the invention does not require $Ca^{++}$ for stability, even at low pH, so addition of calcium salt is generally not needed.

Suitable liquefaction conditions are about 1–60 minutes at about 100°115° C., preferably followed by holding for about 50 minutes to 4 hours at about 80°–100° C. A continuous process is preferred, and the heating is most preferably by jet-cooking.

A dosage level of 2–5 Phadebas U (see below) per gram starch DS (dry substance) is suitable for liquefaction and cyclodextrin formation according to the invention. The starch concentration will usually be in the range 15–40% DS (w/w% dry substance), most often 25–35% DS. A calcium salt may be added to a concentration of 20–100 ppm $Ca^{++}$.

α-amylase catalyzed hydrolysis of starch results in a reduction of viscosity concomitant with an increase in reducing sugars. CGTase also degrades starch, but with essentially no generation of reducing sugars. The enzymatic reactions substantially decrease the degree of polymerization yielding a solution containing high molecular weight maltodextrins along with a substantial content of α-, β-, and γ-cyclodextri. Thus, the conversion of 35% DS corn starch at pH 4.5 from liquefaction at 105° C. for 14 minutes and a hold period at 90° C. for 4 hours into α-, β-, and γ-cyclodextrin is 3.8%, 6.4%, and 3.6%, respectively.

The liquefaction process of the invention may be used for producing dextrose (glucose) in high yield from wet milled corn starch or other refined starch by liquefaction with the CGTase, followed by saccharification with glucoamylase alone or together with pullulanase.

The liquefaction process of the invention may also be used for producing ethanol from starch-containing biomass. In this case the biomass is liquefied with CGTase at a pH of 4.5–5.5, followed by saccharification with glucoamylase to form glucose and simultaneous or subsequent fermentation of the glucose to ethanol with yeast. Thereafter, the alcohol may be recovered by methods known in the art. Preferably, the whole process is carried out at pH around 5.0 without any intermediate pH adjustment, and simultaneous saccharification and fermentation is performed at about 30° C. for up to 72 hours. The liquefaction can be conducted either at low DS levels (15–20%) or high DS levels (20–40%). In the high DS processes, the DS level must be reduced to about 20% prior to fermentation to obtain a maximum yeast tolerance of about 10% alcohol by volume.

The raw material for alcohol production may include refined starch such as wet milled corn starch; raw, unprocessed materials such as corn, wheat, rice, sorghum, cassava and potato (whose starch content range from 15–80%); and other starch containing materials such as waste and by-products from industry. In the case of refined starch, the liquefaction process preferably includes an initial treatment above 100° C. followed by a hold at a lower temperature to complete liquefaction. In the case of other raw materials (with lower starch content), liquefaction is preferably carried out in the range 60°–100° C.

Production of cyclodextrin

The present invention provides processes of using a thermostable CGTase for producing cyclodextrin. The thermostable CGTase is derived from a strain of Thermoanaerobacter or Thermoanaerobium or from a strain of Clostridium. These processes comprise enzymatic treatment of a liquefied starch solution with the CGTase, and recovery of the cyclodextrin from the reaction mixture.

Preferred conditions for the enzymatic conversion to cyclodextrin are pH 5.0–5.5 at above about 60° C., preferably at reaction temperatures exceeding about 70° C., and more preferably exceeding about 85° C. Actually, conversion reaction temperatures exceeding about 70° C. may be needed, e.g. with a CGTase preparation containing glucoamylase (see Example 22). Due to enzyme stability the reaction temperature is preferably below about 90° C.

In a preferred mode of the invention, the process involves liquefaction of a starch slurry with the same CGTase enzyme at about pH 5,0 at an initial treatment temperature exceeding about 100° C. followed by conversion of the liquefied starch to cyclodextrin by maintaining the liquefied starch at about 80°–90° C. in a hold step, desirably without pH adjustment, and desirably without redosing with enzyme.

In contrast to prior-art processes, the process of this invention employs temperatures sufficiently elevated to avoid serious danger of microbial contamination, which is of course advantageous. A separate (but related) advantage is that the enzymatic conversion takes place more quickly with the CGTase at the elevated conversion temperatures. A treatment time not exceeding about 24 hours on an already liquefied starch substrate is contemplated for practice of this invention. Despite the above described advantageous attributes, conversion of already liquefied starch is not a particularly preferred mode of this invention. Far more advantageous is to start the process with raw starch, e.g. a starch slurry, and use the CGTase to generate the liquefied starch therefrom.

The CGTase enzyme may be employed to liquefy starch, (i.e., generate a pourable syrup from a starch slurry) at the pH range 4.0–5.5 in the absence of added calcium and under standard starch liquefaction conditions (as described above). Use of the CGTase to liquefy a starch slurry and then to convert the liquefied starch into cyclodextrin constitutes a most advantageous process and constitutes the preferred practice of the invention.

Liquefaction of the starch with CGTase is accompanied by conversion of the starch into cyclodextrin. Thus, a substantial amount of cyclodextrin has been obtained and is present in the liquefied starch prior to conduct of the further enzymatic conversion of liquefied starch into cyclodextrin.

On the whole, the yield of cyclodextrin available directly from the starch liquefying process is not considered adequate. Further, enzymatic conversion of the liquefied starch with CGTase increases the yield of cyclodextrin substantially.

The elevated temperature hold treatment of the (jet) cooked starch that forms part of the standard conditions starch liquefaction process may be extended about 24 hours, desirably, however, at about 90° C. for converting more of the liquefied starch into cyclodextrin, the conversion step being accompanied by modest dilution of the liquefied starch to a more optimum DS level if desired. Any pH adjustment desired for optimum enzymatic conversion into cyclodextrin may be made either on the initial starch slurry or as an incident to the dilution. However, redosing with more of the CGTase enzyme after the starch liquefaction step has not been found to be necessary.

The thermostability of the cyclodextrin glycosyl transferase of the invention which enables its use at higher enzymatic conversion temperatures than is possible for the prior art enzymes, (notably higher than for the *Bacillus macerans* enzyme whose limiting temperature is 50° C.) allows the combined liquefaction and conversion process to be carried out without a significant intermediate cooling of the syrup. To repeat, this ability to produce cyclodextrin at elevated temperatures avoids the extended reaction times heretofore employed and in practice of this invention, reaction times of not more than about 24 hours are contemplated for the enzymatic conversion of the liquefied starch.

The starch employed in practicing the invention may be obtained from any vegetable source including, for example, waxy maize, corn, waxy maize, wheat, sorghum, potato, tapioca, rice, or sago. In addition to unmodified forms of the starches, modified forms derived from treatment of the starch with enzymes, acids, alkalies, etc. can also be used as substrates. The cyclodextrin production reactions can be performed on liquefied starch at DS concentrations ranging from 1% to 40% DS, but for maximum efficiency of conversion, a 20–30% DS solids solution is preferred. If desired, more concentrated starch slurries may be liquefied (standard conditions being 35% DS), then diluted to 20–30% DS dextrin solutions for conversion into cyclodextrin.

To summarize the terms of an overall process wherein the starting material is raw starch, CGTase of the invention may be employed under a wide range of conditions, including the relatively harsh standard liquefaction conditions of a 35% DS slurry, jet cooking at 105° C. and 90 minute hold at 95° C. over the pH 4.0–5.5 range in the absence of $Ca^{++}$, followed then by a more extensive hold at above 55° C. for up to about 24 hours. For maximum conversion and/or minimum CGTase usage, both hold steps (which can, of course, be a single extended hold) should be conducted within the 80°–90° C. range, and the starch concentration be in the 20–30% DS range (either in the initial starch slurry or through dilution of the liquefied starch).

In further summary, the cyclodextrin can be produced from liquefied starch by incubation of the syrup with CGTase of the invention in the temperature range of 50°–95° C., preferably at 80°–90° C., by reacting for about 24 hours or less in the pH range 4–9 most preferably at about pH 5.0. The cyclodextrin product may be recovered from the reaction solution as heretofore. Moreover, the recovered cyclodextrin can be fractionated into α-, β-, and γ-cyclodextrin according to known to the art practices, e.g. through methods described by D. French et al in Journal of American Chemical Society 71:353 (1949).

The batch conversions of starch hydrolysate into cyclodextrin by the Bacillus macetans CGTase have often been performed heretofore in the presence of a suitable complexant in order to shift the equilibrium in the direction of product formation. Desirably, the cyclodextrin clathrates are insoluble and, therefore, precipitate from solution in the reaction mixture. The complexed cyclodextrin can be recovered by filtration or centrifugation, and the complexant can then be dispelled by methods known to the art. Suitable cyclodextrin complexants include cyclooctane, hexane, 1-butanol, 1-decanol, etc. A number of complexants have been identified that selectively complex with the α- or β-form (see U.S. Pat. No. 3,640,847, for example). In particular, cyclooctane is selective for γ-cyclodextrin while 1-decanol is selective for α-cyclodextrin. Practice of this invention contemplates conducting conversions using CGTase in the presence of complexants.

Cyclodextrin glycosyl transferase assay

The CGTase starch-dextrinizing activity is measured by the Pharmacia Phadebas (R) Amylase Test at pH 6.0, 60° C. by incubating 200 µl of the enzyme solution with 4.0 ml 0.1 M sodium acetate (100 ppm $Ca^{++}$) plus a Phadebas Tablet for 15 minutes. The reaction is then stopped with 0.5 ml 1.0 N HCl.

The assay solution is centrifuged 2 minutes in an Eppendorf centrifuge at room temperature, and the absorbance of the supernatant is read at 620 nm, an absorbance value of 1.0–3.0 should be achieved. A standard curve using *Cacillus licheniformis* α-amylase as the standard was constructed where one Phadebas unit is defined as the amount of enzyme that will catalyze the hydrolysis of 1.0 µmole of glucosidic linkages of Lintner starch per minute at 60° C. pH 6.0.

Quantitation of cyclodextrin product

The yields of α-, β-, or γ-cyclodextrin were determined by BioRad Aminex(R) Carbohydrate HPX-42A High Performance Liquid Chromatography. Two columns (300×7.8 mm) were used in tandem at 85° C. with glass distilled water as the eluent at a flow rate of 0.6 ml/minute. Detection was by refractive index. Standard curves were constructed with authentic samples of α-, β-, and γ-cyclodextrin (Sigma Chemical Company, St. Louis, Miss.).

EXAMPLES

Below, the invention will be described by way of examples. Examples 1–19 relate to CGTase derived from a strain of Thermoanaerobacter or Thermoanaerobium. Examples 20–22 relate to CGTase derived from a strain of Clostridium.

EXAMPLE 1

Production of CGTase by Anaerobic Cultivation

The strain ATCC 53,627 was cultured in a prereduced liquid medium under argon at an initial pH of 7 comprised of the following components in grams per liter: Maltrin M-100, 5.0; $KH_2PO_4$, 2.0; $K_2HPO_4$, 6.0; NaCl, 1.0; $(NH_4)_2SO_4$, 2.5; $MgSO_4 \cdot 7H_2O$, 0.5; $CaCl_2 \cdot 2H_2O$, 0.05; yeast extract, 2.0; $Na_2S$, 0.5; cysteine-CHl, 0.5; resazurin (redox indicator), 2 ng; and trace metals 5.0 ml. The trace metals solution was comprised of the following components in grams per liter: $FeCl_3 \cdot 6H_2O$, 5.40; $ZnSO_4 \cdot 7H_2O$, 1.45; $MnCl_2 \cdot 4H_2O$, 1.00; $CuSO_4 \cdot 5H_2O$, 0.25; and $H_3BO_3$, 0.10. The trace metals solution was acidified with concentrated HCl to dissolve the salts.

The strain was incubated at 67° C. without agitation for 40 hours. The maximal activity level after 40 hours was 200 Phadebas U per liter broth. The culture broth was centrifuged, then filtered, and finally concentrated to a volumetric activity of 30–50 Phadebas U per milliliter by use of a Millipore Minitan System.

Purification of CGTase from ATCC 53,627 was achieved by successive steps involving DEAE-Sepharose chromatography, Chromatofocusing, and acarbose-Sepharose affinity chromatography. DEAE-Sepharose chromatography was performed at pH 7.5 in 10 mM Tris-HCl (2.5 mM $CaCl_2$), 4° C. using a linear NaCl gradient (0–200 mM). Chromatofocusing (Pharmacia) was conducted at 4° C. using a linear pH gradient from pH 7-5. Acarbose affinity chromatography was performed at pH 6.0, 4° C., and elution was achieved by a 0.1 M sodium acetate (100 ppm $Ca^{++}$) buffer wash. Three individual CGTase components designated I, II, and III were obtained by Chromatofocusing, and purified to homogeneity by acarbose affinity chromatography. The relative amounts of the three CGTases following Chromatofocusing were CGTase I–20%, CGTase II–60%, and CGTase III—20%.

EXAMPLE 2

Production of CGTase by Aerobic Cultivation of a Transformed Host Organism

Chromosomal DNA was isolated from cells of the strain ATCC 53,627, as follows. Cells (3.1 g wet weight) were suspended in 4.5 ml 25% sucrose—50 mM Tris pH 8.0– 40 mM EDTA. The suspension was treated with lysozyme (2 mg/ml) for 30 minutes on ice followed by 30 minutes at room temperature. Pronase (1 mg/ml) was added and the suspension was incubated at 37 ° C. for 30 minutes. The lysate was extracted twice with 8 ml phenol for 30 minutes after adding 3 ml 10 mM Tris—1 mM EDTA pH 7.4 buffer, The aqueous phase was then extracted twice with 10 ml chloroform. The DNA was precipitated by adding 0.45 ml 3 M sodium acetate—1 mM EDTA pH 7.0 and 2.75 ml isopropanol and incubating on ice for 5 minutes. The DNA was pelleted by centrifugation and was washed once with 70% ethanol. The pellet was dried for 10 minutes under vacuum and then redissolved in 15 ml 10 mM Tris—1 mM EDTA pH 7.4 buffer.

The DNA preparation was submitted to cesium chloride gradient centrifugation at 15° C., 192,000 g for 40 hours. The chromosomal DNA band was collected, extracted with cesium chloride saturated isopropanol three times, and dialyzed against 10 mM Tris—1 mM EDTA pH 7.4 buffer at 4° C. A total of 590 µg chromosomal DNA was recovered.

The DNA was partially digested with the restriction enzyme EcoRl by incubating 200 µg with 33 units of EcoRl in 150 µl of 50 mM Tris pH 8.0–10 mM $MgCl_2$—100 mM NaCl for 12 minutes at 37° C. The partially digested DNA was submitted to a 10–40% sucrose gradient centrifugation at 135,000 g, 15° C. for 16 hours. Fractions of 180 µl were collected and 5 µl aliquots were analyzed by 1% Agarose gel electrophoresis. Fractions ranging in size from 7 to 15 kb were pooled, dialyzed against 1 l 10 mM Tris—1 mM EDTA pH 7.4 buffer, ethanol precipitated, and dissolved in 100 µl 10 mM Tris—1 mM EDTA pH 7.4 buffer.

The vector pBR322 was digested with EcoRl by incubating 2.5 µg with 30 units of EcoRl in 125 µl of 50 mM Tris pH 8.0–10 mM $MgCl_2$—100 mM NaCl for 2 hours at 37° C. Analysis of the DNA on an Agarose gel showed that the digestion was complete. The digested vector was extracted twice with phenol, once with ether, and ethanol precipitated.

The vector was dissolved in 100 µl of 100 mM Tris pH 8.0–1 mM $MgCl_2$ and dephosphorylated with 20 units of calf intestinal alkaline phosphatase at 37° C. for 30 minutes. The dephosphorylated vector was phenol extracted twice, chloroform extracted twice, and ethanol precipitated. The dephosphorylated pBR322 was dissolved in 50 µl 10 mM Tris—1 mM EDTA pH 7.4 buffer.

Ligation of the digested pBR322 and strain ATCC 53,627 DNA was accomplished by mixing 0.4 µg of the EcoRl partially digested chromosomal DNA (7–15 kb) and 0.1 µg of EcoRl digested, dephosphorylated pBR322 with 10 units T4 DNA ligase in 20 µl 50 mM Tris pH 7.4–10 mM $MgCl_2$—20 mM DTT—1 mM ATP containing 5 µg BSA/ml, and incubating overnight at 14° C.

Competent *E. coli* HB101 (ATCC 33,694) cells were prepared for transformation by the method of T. Maniatus, E. F. Fritsch, and J. Sambrook in Molecular Cloning—A Laboratory manual page 250.

One-half of the ligated DNA prepared above was transformed into competent cells of *E. coli* HB101 according to the method of Maniatus et al. (supra). The cells were cultured overnight at 37 ° C. on plates containing Luria-Bertani (LB) medium and tetracycline at a concentration of 15 µg/ml. The tetracycline-resistant colonies were then replica-plated onto starch plates containing 1% amylopectin-LB medium and tetracycline (15 µg/ml), and incubated overnight at 37° C. CGTase production was determined by exposure of the starch plates after heat-treatment at 70° C. for 1 hour to iodine vapor where clearing zones would be observed.

One CGTase-positive transformant designated *E. coli* NV601 was recovered from over 5000 colonies. The strain was both ampicillin- and tetracycline-resistant. Recovery of the recombinant plasmid by standard alkaline lysis procedures and retransformation of competent *E. coli* HB101 cells yielded CGTase-positive transformants. Restriction mapping of the recombinant plasmid revealed a DNA fragment 12.8 kb in size had been inserted into the EcoRl site of pBR322. Deletion analysis with the restriction enzyme Barnill revealed that the gene encoding the CGTase was located on a 6.0 kb BamHI-BamHI fragment. The CGTase was produced by culturing E. coli NV601 in Luria-Bertani medium containing 15 µg of tetracycline per ml medium at 37° C., 300 rpm for 24 hours. The cells were collected by centrifugation and then lysed by sonication.

Characterization of the recombinant CGTase relative to the native CGTase with respect to molecular weight (SDS-PAGE), isoelectric point, thermostability, action pattern, liquefaction activity, and cyclodextrin production indicated no difference between the enzymes. The recombinant CGTase cross-reacted with antibody raised against the native CGTase (component II).

EXAMPLE 3

Cyclodextrin Production A comparison was made of the cyclodextrin yields produced by CGTase of the invention (ATCC 53,627) and the CGTase from *Bacillus macerans*. Since the *Bacillus macetans* CGTase is unable to liquefy starch under normal jet cooker conditions, a pretreated starch, i.e. Lintner starch was used. The enzymes were reacted with 15% DS Lintner starch (plus 40 ppm $Ca^{++}$) at 50° C. and 90° C., pH 5.0 for 24 hours. The dosage was 4.46 Phadebase U per gram DS starch. The *Bacillus macerans* CFTase was also reacted at pH 7.0 as above to serve as a control.

| CGTase | pH | Temp (°C.) | Cyclodextrin Yield | | | | Total CD g/ 100 ml |
|---|---|---|---|---|---|---|---|
| | | | α-CD | γ-CD | β-CD | Total CD, % | |
| Invention | 5.0 | 50 | 14.9 | 7.0 | 15.3 | 37.2 | 5.6 |
| | 5.0 | 90 | 14.9 | 6.6 | 14.6 | 36.1 | 5.4 |
| Bacillus macerans | 5.0 | 50 | 10.2 | 5.7 | 13.8 | 29.7 | 4.5 |
| | 5.0 | 90 | 0.3 | 0 | 0 | 0.3 | 0.1 |
| | 7.0 | 50 | 10.1 | 5.4 | 14.5 | 30.0 | 4.5 |
| | 7.0 | 90 | 0.5 | 0 | 0.5 | 1.0 | 0.2 |

The results demonstrate that CGTase of the invention gives superior conversion at 50° C., which is optimum for the prior art *B. macerans* enzyme. The CGTase of the invention shows essentially the same high conversion at 90° C., where the prior-art enzyme is seen to be nearly inactive. The CGTase of the invention produces α-, β-, and γ-cylodextrin in a ratio (at 50° C.) of 0.74:1.0:0.41, i.e. relatively more α-CD than the B. macerans enzyme.

EXAMPLE 4

Starch Liquefaction at Various pH

35% DS corn starch with or without 40 ppm $Ca^{++}$ was liquefied at 105° C. for 14 minutes followed by 4 hours at 90° C. Enzyme was dosed at 4.46 Phadebas U/g DS (60° C., pH 6.0). CGTase of the invention (ATCC 53,627) was compared with Termamyl™ (*B. licheniformis* α-amylase, available from Novo Industri A/S) and *B. stearothermophilus* α-amylase (available as G-Zyme™ G995 from Enzyme Bio-Systems, Ltd.).

Dextrose Equivalent (DE) was measured after liquefaction, and the starch was judged as liquefied if the starch syrup after liquefaction was pourable (indicating a substantial viscosity reduction).

| Enzyme | pH | $Ca^{++}$ | DE | Liquefied |
|---|---|---|---|---|
| CGTase | 4.5 | + | 0.51 | Yes |
| CGTase | 4.5 | − | 0.44 | Yes |
| CGTase | 5.0 | + | 0.73 | Yes |
| CGTase | 5.0 | − | 0.69 | Yes |
| CGTase | 5.5 | + | 1.10 | Yes |
| CGTase | 5.5 | − | 0.83 | Yes |
| BS Amylase | 4.5 | + | Not determinable | No |
| BS Amylase | 4.5 | − | Not determinable | No |
| BS Amylase | 5.0 | + | 4.78 | Yes* |
| BS Amylase | 5.0 | − | Not determinable | No |
| BS Amylase | 5.5 | + | 9.78 | Yes |
| BS Amylase | 5.5 | − | 5.58 | Yes |
| BS Amylase | 5.8 | + | 13.6 | Yes |
| Termamyl ™ | 6.2 | + | 14.4 | Yes |

*Rated as liquefied, but very viscous.

It is seen that good liquefaction can be achieved with CGTase of the invention, even at pH as low as 4.5 without $Ca^{++}$ addition, and essentially without formation of reducing sugars.

EXAMPLE 5

Starch Liquefraction at Various Enzyme Dosages

Figure 6:
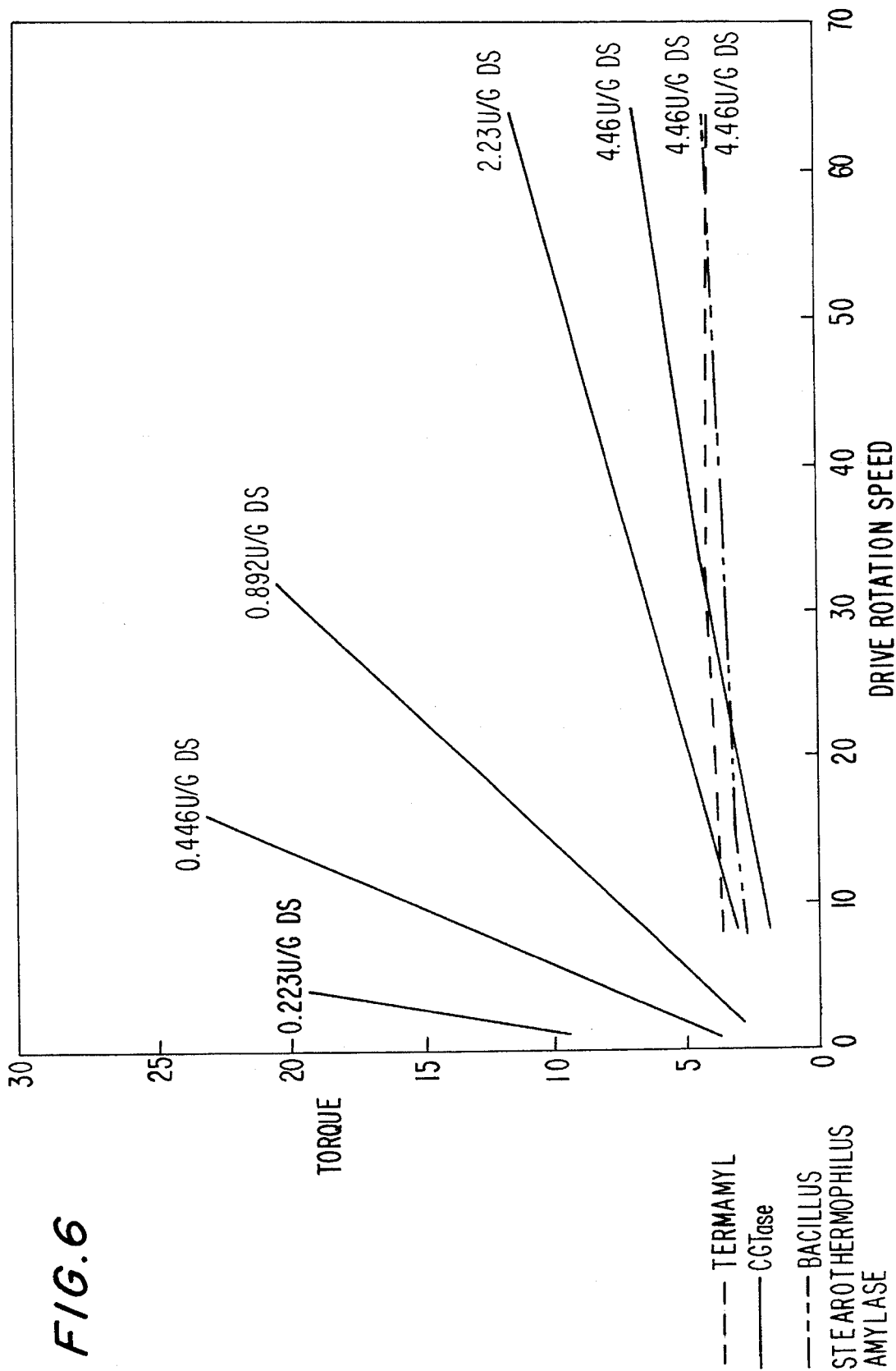
FIG. 6 illustrates a plot of torque versus rotation speed measurement demonstrating the variations in viscosity of liquefied starch solutions obtained with varying dosage levels of CGTase.

DS corn starch was liquefied with CGTase (ATCC 53,627) at pH 4.5 in the absence of added $Ca^{++}$. Enzyme dosages of 0.223, 0.446, 0,892, 2.23 and 4.46 Phadebas U/g DS were used. For comparison, Termamyl was used at pH 6.2 and *B. stearothermophilus* amylase at pH 5.8, both at 4.46 U/g DS and with 40 ppm $Ca^{++}$ present. Liquefaction conditions were 14 minutes at 100° C. or 105° C. (as indicated below), followed by 4 hours at 90° C. After liquefaction, viscosity was measured at 60° C. with a Haake Rotovisco RV 12 viscometer with NV sensor system and M500 measuring drive unit at the respective pHs of liquefaction. Results are given below and shown in FIG. 6.

| Enzyme | Dosage U/g DS | Added $Ca^{++}$ | pH | Primary Liq. temp. | Viscosity (CP) at drive rot. speed 32 |
|---|---|---|---|---|---|
| CGTase | 0.223 | — | 4.5 | 100° C. | *) |
| CGTase | 0.446 | — | 4.5 | 100° C. | *) |
| CGTase | 0.892 | — | 4.5 | 105° C. | 208 |
| CGTase | 2.23 | — | 4.5 | 105° C. | 66.9 |
| CGTase | 4.46 | — | 4.5 | 105° C. | 42.4 |
| Termamyl | 4.46 | 40 ppm | 6.2 | 105° C. | 41.6 |
| BS amylase | 4.46 | 40 ppm | 5.8 | 105° C. | 34.1 |

*)measurement not possible at this speed

EXAMPLE 6

Saccharification of Liquefied Starch The liquefied starches of example 4 were adjusted to pH 4.3 or 4.5 at 60° C., and Dextrozyme™ 150/50 was added at a dosage of 1.2 l/t DS. Dextrozyme is a mixture of glucoamylase from *Aspergillus niger* and pullulanase from *Bacillus acidopullulyticus*; it is available from Novo Industri A/S. Saccharification was performed for 48 hours at 60° C., and dextrose was determined by Bio-Rad Aminex® HPX-87C HPLC.

| Enzyme | Liq. pH | Sacch. pH | $Ca^{++}$ | % Dextrose |
|---|---|---|---|---|
| CGTase | 4.5 | 4.5 | + | 96.0 |
| CGTase | 4.5 | 4.5 | − | 96.0 |
| CGTase | 5.0 | 4.3 | + | 95.6 |
| CGTase | 5.0 | 4.3 | − | 95.5 |
| CGTase | 5.5 | 4.3 | + | 95.7 |
| CGTase | 5.5 | 4.3 | − | 95.8 |
| BS Amylase | 4.5 | 4.3 | + | Not determinable |
| BS Amylase | 4.5 | 4.3 | − | Not determinable |
| BS Amylase | 5.0 | 4.3 | + | 96.0 |
| BS Amylase | 5.0 | 4.3 | − | Not determinable |
| BS Amylase | 5.5 | 4.3 | + | 95.8 |
| BS Amylase | 5.5 | 4.3 | − | 95.9 |
| BS Amylase | 5.8 | 4.5 | + | 96.8 |
| Termamyl ™ | 6.2 | 4.5 | + | 96.4 |

The results show good saccharification of all starches liquefied according to the invention. The ability to saccharify the pH 4.5 liquefied starch demonstrates a clear process advantage of this invention over prior-art liquefactions with α-amylase from *B. licheniformis* or *B. stearothermophilus* since little or no pH adjustment prior to saccharification is necessary in case of starch liquefaction according to the invention.

EXAMPLE 7

Production of Cyclodextrin at Various Starch Concentrations The corn starch was varied from 15% to 40% DS. The slurries were first liquefied at pH 5.0 without added calcium by a 14 minute treatment at 105° C. followed by a 4 hour hold at 90° C., using the CGTase (ATCC 53,627) at a dose of 4.46 Phadebas U per gram DS starch. The production of cyclodextrin was monitored after continuing the hold portion of the starch liquefaction process so as to incubate the enzyme containing dextrin solution for an additional 24 hours at pH 5.0 and 90° C. Cyclodextrin yields were determined by Bio-Rad Aminex Carbohydrate HPX-42A HPLC. Results:

| | Cyclodextrin yield | | | | |
|---|---|---|---|---|---|
| % DS | α-CD % | γ-CD % | β-CD % | Total CD % | Total CD g/100 ml |
| 15 | 9.6 | 6.3 | 15.4 | 31.3 | 4.7 |
| 20 | 8.1 | 5.8 | 17.6 | 31.5 | 6.3 |
| 25 | 7.2 | 5.9 | 15.3 | 28.4 | 7.1 |
| 30 | 6.7 | 4.6 | 12.6 | 23.9 | 7.2 |
| 35 | 5.0 | 4.2 | 11.0 | 20.2 | 7.1 |
| 40 | 6.9 | 4.4 | 11.1 | 22.4 | 9.0 |

It was concluded that an initial starch concentration of about 20–30% was optimal for the production of cyclodextrin, based on Total % CD and g CD/100 ml. A concentration of 25% DS was therefore chosen for further examples. β-cyclodextrin was primarily produced at all starch concentrations. The ratio of β:α:γcyclodextrin was 1.0.:0.47:0.39 at 25% DS. The highest observed yield of cyclodextrin from 25% DS starch was approximately 30%.

Redosing with the CGTase enzyme and extending the reaction time to 48 hours did not increase the yields.

EXAMPLE 8

Production of Cyclodextrin at Various pH The effect of pH on cyclodextrin production was determined using a 25% DS corn starch slurry. The starch slurries were liquefied at the indicated pH values, but otherwise as in Example 7, and the liquefied starches were then incubated 24 hours at 90° C. at the same pH values.

The results, shown below, indicate that pH 5.0 was optimal for the combined process of starch liquefaction and cyclodextrin production.

| | Cyclodextrin Yield | | | | |
|---|---|---|---|---|---|
| pH | α-CD % | γ-CD % | β-CD % | Total CD % | Total CD g/100 ml |
| 4.0 | 2.5 | 1.0 | 2.0 | 5.5 | 1.4 |
| 4.5 | 5.0 | 4.3 | 8.4 | 17.7 | 4.4 |
| 5.0 | 7.4 | 5.5 | 16.7 | 29.6 | 7.4 |
| 6.0 | 8.0 | 5.3 | 14.9 | 28.2 | 7.1 |
| 7.0 | 8.4 | 5.0 | 12.9 | 26.3 | 6.6 |
| 8.0 | 8.4 | 5.0 | 13.4 | 26.8 | 6.7 |
| 9.0 | 6.3 | 4.5 | 8.5 | 19.3 | 4.8 |

EXAMPLE 9

Production of Cyclodextrin at Various Temperatures

The effect of temperature on cyclodextrin production by CGTase of the invention (ATCC 53,627) was examined in the absence of added calcium by conduct of the incubation step for 24 hours at pH 5.0 at various temperatures, as indicated below. A 15% DS or 25% DS slurry of corn starch was first liquefied with the CGTase under the conditions of Example 7 at a dose of 4.46 Phadebas U per gram DS starch. Results:

| | 15% DS Cyclodextrin Yield | | | | |
|---|---|---|---|---|---|
| Temperature °C. | α-CD % | γ-CD % | β-CD % | Total CD % | Total CD g/100 ml |
| 50 | 8.1 | 5.6 | 15.4 | 29.0 | 4.4 |
| 80 | 8.6 | 6.1 | 18.7 | 33.4 | 5.0 |
| 90 | 9.6 | 6.3 | 15.4 | 31.3 | 4.7 |
| 95 | 7.3 | 5.1 | 8.5 | 20.9 | 3.1 |

| | 25% DS Cyclodextrin Yield | | | | |
|---|---|---|---|---|---|
| Temperature °C. | α-CD % | γ-CD % | β-CD % | Total CD % | Total CD g/100 ml |
| 50 | 7.1 | 4.8 | 12.1 | 24.0 | 6.0 |
| 70 | 7.2 | 5.5 | 13.7 | 26.4 | 6.6 |
| 80 | 7.2 | 5.5 | 14.6 | 27.3 | 6.8 |
| 90 | 7.2 | 5.9 | 15.3 | 28.4 | 7.1 |
| 95 | 6.3 | 5.8 | 14.6 | 26.7 | 6.7 |

The results show a conversion temperature of 80°–90° C. to be optimal, both at 15% DS and 25% DS (after a 24 hour incubation). Lowering the temperature to 50° C. produced a lesser yield.

EXAMPLE 10

Production of Cyclodextrin at High Temperature with and without Redosing of Enzyme.

The possibility that equilibrium had not been achieved was examined at 90° C. and 95° C. by redosing the reaction mixtures of Example 9 involving 15% DS starch with CGTase prior to the 24 hours incubation, and allowing the reaction to continue an additional 24 hours. The results (see below) demonstrated that at 90° C. equilibrium had been reached. At 95° C., redosing was necessary to achieve the same yields of cyclodextrin indicating thereby some loss of enzyme activity during prolonged incubation at 95° C.

| | | | Cyclodextrin Yield | | | | |
|---|---|---|---|---|---|---|---|
| Temp. (°C.) | Redose | Time (Hours) | α-CD % | γ-CD % | β-CD % | Total CD % | Total CD g/100 ml |
| 90 | – | 24 | 9.6 | 6.3 | 15.4 | 31.3 | 4.7 |
| 90 | + | 24 | 9.5 | 6.3 | 16.2 | 32.0 | 4.8 |
| 90 | – | 48 | 10.1 | 6.3 | 14.0 | 30.4 | 4.6 |
| 90 | + | 48 | 9.1 | 5.9 | 16.5 | 31.5 | 4.7 |
| 95 | – | 24 | 7.3 | 5.1 | 8.5 | 20.9 | 3.1 |
| 95 | + | 24 | 10.2 | 6.5 | 13.7 | 30.4 | 4.6 |

| Temp. (°C.) | Redose | Time (Hours) | α-CD % | γ-CD % | β-CD % | Total CD % | Total CD g/100 ml |
|---|---|---|---|---|---|---|---|
| 95 | − | 48 | 9.3 | 5.2 | 10.2 | 24.7 | 3.7 |
| 95 | + | 48 | 11.3 | 6.6 | 13.5 | 31.4 | 4.7 |

EXAMPLE 11

Production of Cyclodextrin with and without Calcium Addition The effect of calcium on cyclodextrin production was investigated. A 25% DS corn starch slurry was liquefied with CGTase of the invention (ATCC 53,627) at pH 5.0 in the presence and absence of 40 ppm calcium at a dose of 4.46 Phadebas U per gram DS starch. The liquefied starches were then incubated 24 hours at 90° C. The results (see below) indicated that presence of calcium ion had no effect on the overall yield.

| Calcium | α-CD % | γ-CD % | β-CD % | Total CD % | Total CD g/100 ml |
|---|---|---|---|---|---|
| − | 6.0 | 6.0 | 15.1 | 27.1 | 6.8 |
| + | 6.2 | 5.8 | 14.4 | 26.4 | 6.6 |

EXAMPLE 12

Production of Cyclodextrin at Various Enzyme Dosages

The effect of varying the CGTase dose on cyclodextrin yield was determined using 25% DS corn starch. The dose was varied from 2.23 to 6.69 Phadebas U per gram DS starch. The starch was liquefied at pH 5.0 using the doses given above in the absence of added calcium with the CGTase of ATCC 53,627. The liquefied starches were then incubated 24 or 48 hours at 90° C., pH 5.0. Other conditions were as in example 5.

The results (see below) demonstrated that after 24 hours and 48 hours, the highest yields were achieved at doses of 4.46 and 3.35 Phadebas U per gram DS starch.

| Dose, Phadebas U per gram DS | Time, hours | α-CD % | γ-CD % | β-CD % | Total CD % | Total CD g/100 ml |
|---|---|---|---|---|---|---|
| 2.23 | 24 | 5.8 | 5.9 | 13.0 | 24.7 | 6.2 |
| 3.35 | 24 | 6.3 | 5.8 | 14.9 | 27.0 | 6.8 |
| 4.46 | 24 | 6.0 | 6.0 | 15.1 | 27.1 | 6.8 |
| 6.69 | 24 | 5.9 | 5.2 | 10.5 | 21.6 | 5.4 |
| 2.23 | 48 | 6.7 | 6.7 | 14.8 | 28.2 | 7.1 |
| 3.35 | 48 | 6.7 | 6.5 | 15.3 | 28.5 | 7.1 |
| 4.46 | 48 | 6.7 | 6.1 | 15.8 | 28.6 | 7.1 |
| 6.69 | 48 | 6.6 | 5.6 | 13.7 | 25.9 | 6.5 |

EXAMPLE 13

Production of Cyclodextrin Using Complexant

The effect of cyclooctane as a β-cyclodextrin complexant in the conversion of cyclodextrin was investigated. A 25% DS corn starch slurry was liquefied at pH 5.0 in the absence of added calcium with the CGTase of ATCC 53,627 under the conditions of example 7 at a dose of 4.46 Phadebas U per gram DS starch. Then followed a conversion to cyclodextrin at 90° C. for 24 hours, but cyclooctane was added at a level of 0.6 gram per gram DS starch prior to commencing the 24 hour incubation.

The conversion results (see below) demonstrated that the addition of cyclooctane increased the final cyclodextrin yield, particularly that of β-cyclodextrin.

| | α-CD % | γ-CD % | β-CD % | Total CD % | Total CD g/100 ml |
|---|---|---|---|---|---|
| Control | 7.2 | 5.9 | 15.3 | 28.4 | 7.1 |
| With cyclooctane: | | | | | |
| Uncomplexed | 3.7 | 2.3 | 2.6 | 8.6 | 2.2 |
| Complexed | 1.9 | 0.6 | 25.0 | 27.5 | 6.9 |
| Total | 5.6 | 2.9 | 27.6 | 36.1 | 9.1 |

EXAMPLE 14

Production of Cyclodextrin from Various Starches

A comparison of several starches was made. Slurries (25% DS) of starch from corn, potatoes, wheat, rice, and waxy maize were liquefied at pH 5.0 in the absence of added calcium with CGTase of the invention (ATCC 53,627) at a dose of 4.46 Phadebas U per gram DS starch under the conditions of Example 7. The liquefied starch solutions were then incubated 24 hours at 90° C.

The results (see below) showed that there were differences in the final cyclodextrin yield and that β-cyclodextrin was the primary product formed in all cases.

| Starch | α-CD % | γ-CD % | β-CD % | Total CD % | Total CD g/100 ml |
|---|---|---|---|---|---|
| Corn | 7.4 | 5.4 | 15.4 | 28.2 | 7.1 |
| Potato | 9.3 | 5.6 | 14.6 | 29.5 | 7.4 |
| Wheat | 7.0 | 4.9 | 13.7 | 25.6 | 6.4 |
| Rice | 5.1 | 4.3 | 8.3 | 17.7 | 4.4 |
| Waxy Maize | 7.1 | 4.5 | 11.9 | 23.5 | 5.9 |

EXAMPLE 15

Ethanol Fermentation of Liquefied Starch

A 31.5% DS slurry of wet-milled corn starch was liquefied with CGTase of the invention (ATCC 53,627) at pH 5.0 without added calcium for 14 minutes at 105° C. followed by 4 hours at 90° C. A control with Termamyl™ was also performed as described except at pH 6.2 in the presence of 40 ppm calcium. The enzyme dose in each case was 5.0 Phadebas units per gram DS starch.

At the end of liquefaction, the thinned starch was diluted to 22.4% DS with a yeast nutrient mix. The final concentration of the components in the nutrient mix per liter were 4.0 g yeast extract, 1.6 g ammonium phosphate, 0.4 g magnesium sulfate, 3.2 g citric acid, and 0.6 g sodium citrate. The final pH was 5.2. AMG 200 L (NOVO Laboratories, Inc., Danbury, CT) was added at a dose of 0.44% wt/wt based on the starch. Penicillin G and streptomycin sulfate were included at levels of 200 μg/ml. The fermentations were incubated at 30° C., 300 rpm for 64 hours.

The production of ethanol was indirectly measured by carbon dioxide production, i.e. weight loss as a function of time. The final ethanol yields were confirmed by Bio-Rad Aminex HPX-42A High Performance Liquid Chromatography.

After 64 hours, the yield of ethanol based on carbon dioxide production was 87.3% and 89.7% for CGTase and Termamyl liquefied starches, respectively. These yields were confirmed by Bio-Rad Aminex HPX-42A HPLC. The industrial standard yield is generally about 86–90%.

EXAMPLE 16

Production of CGTase by Anaerobic Cultivation of NCIB 40,053–40,059

Strains NCIB 40,053 through 40,053 were cultured as described in Example 1 except that cultivation temperature was 55° C.

The maximal activity level after about 40 hours of incubation in Phadebas units per liter broth was as follows: NCIB 40,053:18, NCIB 40,054: 53, NCIB 40,055: 26, NCIB 40,056: 22, NCIB 40,057: 27, NCIB 40,058: 78, and NCIB 40,059: 10. The culture broths were centrifuged, then filtered, and finally concentrated to a volumetric activity of 30–50 Phadebas units per milliliter by use of a Millipore Minitan System.

EXAMPLE 17

Starch Liquefaction with CGTase of NCIB 40,053–40,059

The CGTase preparations prepared as in example 16 were compared as to their ability to liquefy 35% DS corn starch at pH 4.5. The starch was liquefied at 105° C. for 14 minutes followed by 4 hours at 90° C. at an enzyme dose of 4.46 Phadebas U/g DS (60° C., pH 6.0).

Dextrose Equivalent (DE) was measured after liquefaction, and the starch was judged as liquefied if the starch syrup after liquefaction was pourable indicating a substantial reduction in viscosity.

The results indicated that all the CGTases could achieve good liquefaction at pH 4.5 similar to the CGTase from strain ATCC 53,627. In all cases, essentially no DE was measurable indicative of CGTase activity.

Aminex® HPX-42A (Bio-Rad) HPLC using refractive index for detection demonstrated that the action patterns produced from liquefaction of the corn starch were typical of a CGTase where the three peaks were α-, γ-, and β-cyclodextrin. No major differences in the relative ratio of the cyclodextrin produced by each enzyme were observed compared to the CGTase of ATCC 53,627.

EXAMPLE 18

Liquefaction with Cloned CGTase

A 35% DS corn starch slurry was treated with cloned CGTase prepared as in example 2 at a dosage of 8.92 Phadebas units per g DS at pH 4.5 without added $Ca^{++}$. Jetting was done at 105° C. for 5 minutes (primary liquefaction) followed by a hold at 95° C. for 2 hours or 90° C. for 4 hours (secondary liquefaction). During secondary liquefaction at 95° C. or 90° C., a rapid reduction in viscosity was observed. At 90° C., the viscosity reduction was monitored over time using a Nametre viscometer. The results demonstrated that there was a rapid reduction in viscosity to 400 centipoise×g/cm$^3$ by 7 minutes into secondary liquefaction. The action patterns of the liquefied starches after secondary liquefaction determined by Bio-Rad Aminex® HPX-42A HPLC demonstrated the characteristic cyclodextrin pattern at both temperatures. DE values of <1.0 were obtained by the neocuproine method indicating the absence of reducing end-groups consistent with the mechanism of a CGTase.

EXAMPLE 19

Saccharification of Starch Liquefied with Cloned CGTase

The starch solutions liquefied with CGTase at pH 4.5 in example 18 were saccharified with AMG and Dextrozyme at pH 4.5, 60° C. for 48 hours at a dose of 0.18 AG per g DS. Dextrose yields were determined by Bio-Rad Aminex® HPX-87C HPLC.

| Secondary liquefaction temperature | Enzyme | % Yield | | | |
|---|---|---|---|---|---|
| | | Dextrose | DP2 | DP3 | DP4 |
| 95° C. | Dextrozyme | 95.87 | 2.44 | 0.39 | 1.30 |
| | AMG | 95.09 | 2.27 | 0.36 | 2.28 |
| 90° C. | Dextrozyme | 95.37 | 3.34 | 0.40 | 0.89 |
| | AMG | 95.36 | 3.21 | 0.38 | 1.05 |

The results show a good yield of dextrose in all cases. The highest yield was achieved with secondary liquefaction at 95° C. and saccharification with Dextrozyme.

EXAMPLE 20

Cyclodextrin production The ability of the CGTases to produce cyclodextrin was determined at 25% DS. The slurries were liquefied by a 14 minute treatment at 105° C. followed by a 4 hour hold at 90° C. using an enzyme dose of 4.46 Phadebas unit per gram DS starch in the presence of 40 ppm $Ca^{++}$. The production of cyclodextrin was achieved by incubating the solution an additional 24 hours at 90° C. Liquefaction and cyclodextrinization were performed at pH 5.5 with the C. thermoamylolyticum CGTase and at pH 5.0 with the C. thermohydrosulfuricum CGTase.

The results, shown below, indicate that both Clostridium CGTases were primarily β-cyclodextrin producers with 25% DS corn starch, but that the C. thermoamylolyticum CGTase was more effective in producing cyclodextrin than the C. thermohydrosulfuricum CGTase.

|  |  |  | Yield g/100 ml | | | |
| --- | --- | --- | --- | --- | --- | --- |
| CGTase | % DS | % yield | Alpha | Beta | Gamma | Total |
| C. thermoamylolyticum | 25 | 16.8 | 1.09 | 2.00 | 1.10 | 4.19 |
| C. thermohydrosulfuricum | 25 | 8.4 | 0.74 | 0.91 | 0.44 | 2.09 |

EXAMPLE 21

Effect of starch pretreatment on cyclodextrin yield

The effect of starch pretreatment on cyclodextrin yield was examined using Maltodextrin M50 and Maltodextrin M100 at concentrations of 25% DS. The production of cyclodextrin was accomplished by incubating the maltodextrin solutions for 24 hours at 90° C. using an enzyme dose of 4.46 Phadebas units per gram DS maltodextrin in the presence of 40 ppm $Ca^{++}$. Cyclodextrinization was performed at pH 5.5 with the C. thermoamylolyticum CGTase and at pH 5.0 with the C. thermohydrosulfuricum CGTase.

The results (see Table III) demonstrate that by using preliquefied starch, i.e., Maltodextrin M50, the cyclodextrin yields produced by the C. thermohydrosulfuricum thermohydrosulfuricum CGTase can be substantially increased. In both cases, as the DE increases the total cyclodextrin yield decreases.

| Effect of starch pretreatment on cyclodextrinization | | | | | | | | |
| --- | --- | --- | --- | --- | --- | --- | --- | --- |
| | | | | | Yield g/100 ml | | | |
| CGTase | Maltodextrin | Treatment | DE | % yield | Alpha | Beta | Gamma | Total |
| C. thermoamylolyticum | M50 | Acid | 7.0 | 18.0 | 1.20 | 2.36 | 0.94 | 4.50 |
| | M100 | Acid/Enzyme | 12.0 | 9.2 | 0.51 | 1.56 | 0.23 | 2.30 |
| C. thermohydrosulfuricum | M50 | Acid | 7.0 | 17.8 | 1.16 | 2.51 | 0.80 | 4.47 |
| | M100 | Acid/Enzyme | 12.0 | 8.8 | 0.50 | 1.53 | 0.16 | 2.19 |

EXAMPLE 22

The effect of reaction temperature

The enzyme preparations from C. thermoamylolyticum ATCC 39,252 and C. thermohydrosulfuricum ATCC 53,016 were employed to treat a 20% DS, 90 fluidity corn starch at pH 4.5 (American Maize, Hammond, Ind.), 70° C. for 24 hours in the presence of 200 ppm $Ca^{++}$. The enzyme dose was 100 Phadebas units/g DS. The action patterns were determined by Bio-Rad Aminex® HPX-42A HPLC. Dextrose equivalents (DE) were measured by the neocuproine method.

Figure 12:
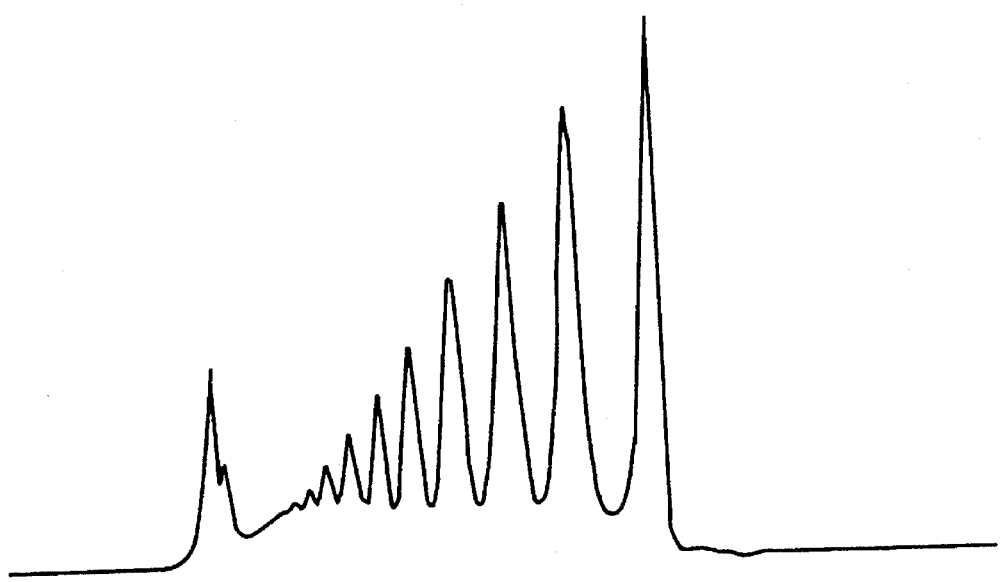
FIG. 12 is an HPLC plot showing the action pattern of CGTase from *Clostridium thermoamylolyticum* ATCC 39,252 on a pre-liquefied corn starch (DE 33).
Figure 13:
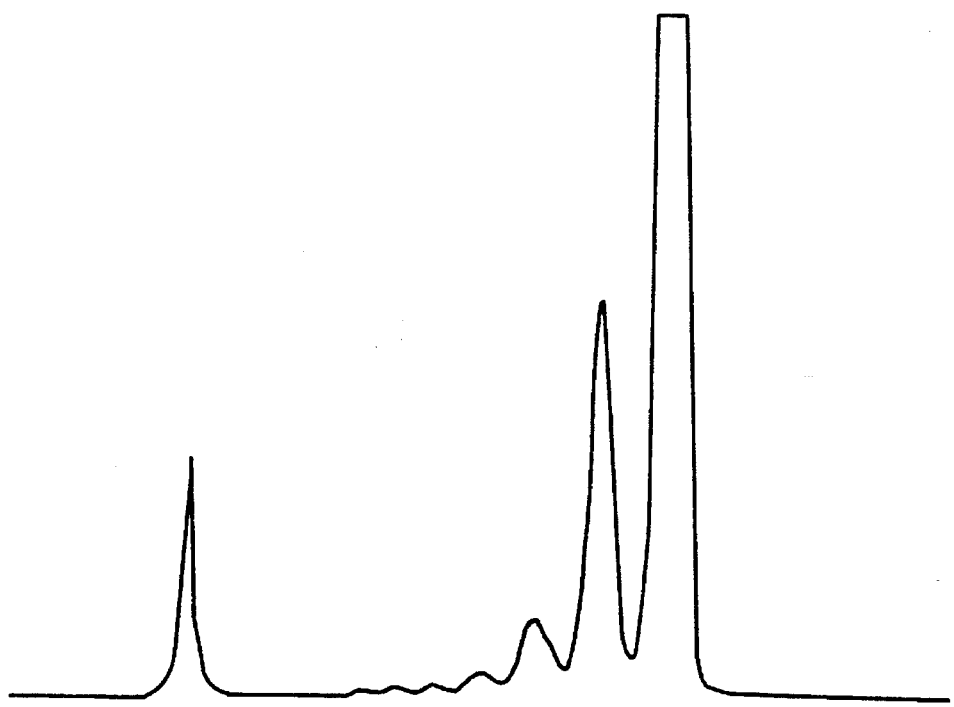
FIG. 13 is an HPLC plot showing the action pattern of CGTase from *Clostridium thermohydrosulfuricum* ATCC 53,016 on a pre-liquefied corn starch (DE 68).

The action patterns as illustrated in FIGS. 12 and 13 clearly suggest the presence of a glucoamylase-like activity in each preparation. This is further confirmed by the DE measurements.

The action patterns and DE (see FIGS. 12 and 13) are consistent with the data reported by U.S. Pat. No. 4,578,352 at the same pH, conversion temperature, and DS levels. Little or no cyclodextrin product is to be found in the 70° C. hydrolysate. The temperature of 90° C. employed in Examples 20 and 21 inactivates any glucoamylase activity in each preparation.

We claim:

1. An isolated thermostable cyclodextrin glycosyl transferase derived from Thermoanaerobacter or Thermoanaerobium having the following properties:

(a) a temperature optimum of about 95° C. measured at pH 5;

(b) a pH optimum of about 5.0; and (c) a residual activity of about 95% after 40 minutes incubation at 80° C. and pH 5.0 in the absence of starch and $Ca^{++}$.

2. The thermostable cyclodextrin glycosyl transferase according to claim 1 which has a molecular weight determined by SDS-polyacrylamide gel electrophoresis between about 99,000 and about 210,000 daltons.

3. The thermostable cyclodextrin glycosyl transferase according to claim 1 which is derived from a strain selected from the group consisting of NCIB 40,053, 40,054, 40,055, 1,056, 40,057, 49,058 and 40,059 and ATCC 53,627.

4. An isolated thermostable cyclodextrin glycosyl transferase having the following properties:

(a) a temperature optimum of about 95° C. measured at pH 5;

(b) a pH optimum of about 5.0; and (c) a residual activity of about 95% after 40 minutes incubation at 80° C. and pH 5.0 in the absence of starch and $Ca^{++}$;

which is produced by cultivating a Thermoanaerobacter or Thermoanaerobium strain selected from the group consisting of NCIB 40,053, 40,054, 40,055, 40,056, 40,057, 40,058 and 40,059 and ATCC 53,627.

5. An isolated thermostable cyclodextrin glycosyl transferase having the following properties:

(a) a temperature optimum of about 95° C. measured at pH 5;

(b) a pH optimum of about 5.0; and (c) a residual activity of about 95% after 40 minutes incubation at 80° C. and pH 5.0 in the absence of starch and Ca++;

which is produced by cultivating a host organism which is transformed with a DNA sequence encoding said cyclodextrin glycosyl transferase, wherein said DNA sequence is derived from a Thermoanaerobacter or Thermoanaerobium strain selected from the group consisting of NCIB 40,053, 40,054, 40,055, 40,056, 40,057, 40,058 and 40,059 and ATCC 53,627.

* * * * *